(12) United States Patent
Otani et al.

(10) Patent No.: US 7,001,677 B2
(45) Date of Patent: Feb. 21, 2006

(54) ELECTROLUMINESCENT DEVICES COMPRISING DIKETOPYRROLOPYRROLES

(75) Inventors: Junji Otani, Kobe (JP); Hiroshi Yamamoto, Takarazuka (JP); Norihisa Dan, Kyoto (JP); Abul Iqbal, Arconciel (CH); Robert Moretti, Petit-Lancy (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 8 days.

(21) Appl. No.: 10/425,201

(22) Filed: Apr. 29, 2003

(65) Prior Publication Data

US 2004/0009368 A1    Jan. 15, 2004

Related U.S. Application Data

(62) Division of application No. 09/657,738, filed on Sep. 8, 2000.

(30) Foreign Application Priority Data

Sep. 27, 1999 (EP) .................................. 99810868

(51) Int. Cl.
H05B 33/14 (2006.01)
C09K 11/06 (2006.01)

(52) U.S. Cl. .................. 428/690; 428/917; 313/504; 313/506; 252/301.16

(58) Field of Classification Search ................ 428/690, 428/917; 313/504, 506; 252/301.16, 301.35
See application file for complete search history.

(56) References Cited

U.S. PATENT DOCUMENTS

| 4,585,878 A | 4/1986 | Jost et al. ................... 548/453 |
| 5,298,063 A | 3/1994 | Mizuguchi et al. ........... 106/21 |
| 5,973,146 A | 10/1999 | Rochat et al. ............... 544/144 |
| 6,603,020 B1 * | 8/2003 | Moretti et al. .............. 548/453 |
| 6,805,978 B1 * | 10/2004 | Murase et al. .............. 428/690 |

FOREIGN PATENT DOCUMENTS

| DE | 3713459 | 8/1988 |
| EP | 0456610 | 11/1991 |
| EP | 0 499 011 | 8/1992 |
| EP | 0542669 | 5/1993 |
| EP | 0 563 009 | 9/1993 |
| EP | 0 811 625 | 12/1997 |
| EP | 1087005 | 3/2001 |
| WO | 96/08537 | 3/1996 |
| WO | 98/25927 | 6/1998 |
| WO | 98/32802 | 7/1998 |

OTHER PUBLICATIONS

Patent Abst. of Japan Publication No. 09003448 (Jan. 1997).
Patent Abst. of Japan Publication No. 05320633 (Dec. 1993).
Patent Abst. of Japan Publication No. 02296891 (Dec. 1990).

* cited by examiner

*Primary Examiner*—Marie Yamnitzky
(74) *Attorney, Agent, or Firm*—Shiela A. Loggins

(57) ABSTRACT

Electroluminescent device comprising in this order
(a) an anode
(b) a hole transporting layer
(c) a light-emitting layer
(d) optionally an electron transporting layer and
(e) a cathode
and a light-emitting substance, wherein the light-emitting substance is a diketopyrrolopyrrole represented by formula I or formula III

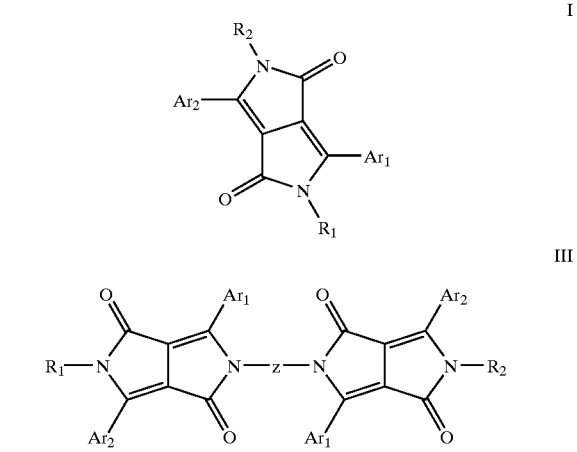

processes for the preparation of compounds I, its uses and compositions comprising the compounds I and/or III.

7 Claims, No Drawings

ELECTROLUMINESCENT DEVICES COMPRISING DIKETOPYRROLOPYRROLES

This application is a divisional of application Ser. No. 09/657,738, filed on Sep. 8, 2000.

The present invention relates to an electroluminescent device comprising in this order
(a) an anode
(b) a hole transporting layer
(c) a light-emitting layer
(d) optionally an electron transporting layer and
(e) a cathode and a light-emitting substance, wherein the light-emitting substance is a diketopyrrolopyrrole ("DPP") represented by formula I or formula III

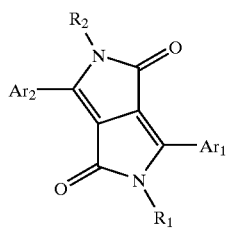

I

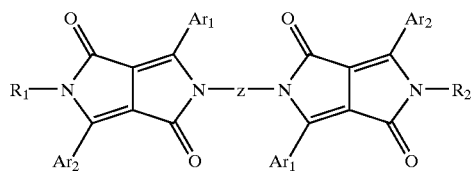

III wherein $R_1$ and $R_2$, independently from each other, stand for $C_1$–$C_{25}$-alkyl, allyl which can be substituted one to three times with $C_1$–$C_3$alkyl or $Ar_3$, or —$CR_3R_4$—$(CH_2)_m$—$Ar_3$, wherein $R_3$ and $R_4$ independently from each other stand for hydrogen or $C_1$–$C_4$alkyl, or phenyl which can be substituted one to three times with $C_1$–$C_3$ alkyl, $Ar_3$ stands for phenyl or 1- or 2-naphthyl which can be substituted one to three times with $C_1$–$C_8$alkyl, $C_1$–$C_8$alkoxy, halogen or phenyl, which can be substituted with $C_1$–$C_8$alkyl or $C_1$–$C_8$alkoxy one to three times, and m stands for 0, 1, 2, 3 or 4, $Ar_1$ and $Ar_2$, independently from each other, stand for aryl radicals, preferably for

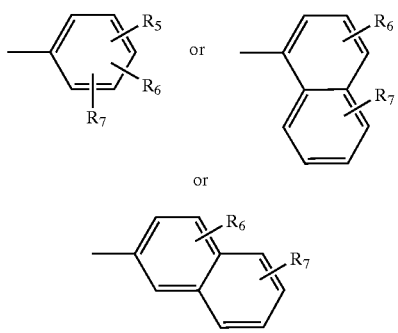

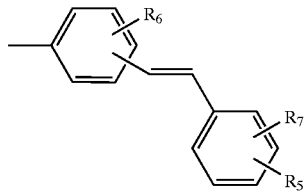

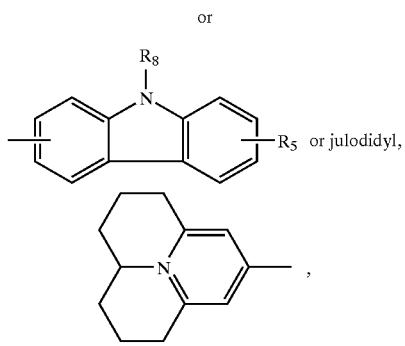

which can be substituted one to four times with $C_1$–$C_4$alkyl, $C_1$–$C_4$alkoxy, or phenyl

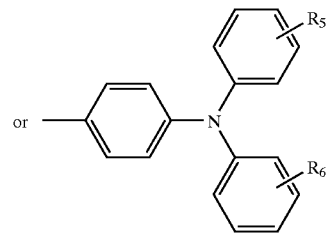

wherein
$R_5$, $R_6$ and $R_7$, independently from each other, stand for hydrogen, cyano, halogen, $C_1$–$C_6$alkyl, —$NR_8R_9$, —$OR_{10}$, —$S(O)_nR_8$, —$Se(O)_nR_8$, or phenyl, which can be substituted one to three times with $C_1$–$C_8$alkyl or $C_1$–$C_8$alkoxy, wherein $R_8$ and $R_9$, independently from each other, stand for hydrogen, phenyl, $C_1$–$C_{25}$-alkyl, $C_5$–$C_{12}$-cycloalkyl, —$CR_3R_4$—$(CH_2)_m$-Ph, $R_{10}$, wherein $R_{10}$ stands for $C_6$–$C_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, wherein Ph, the aryl and heterocyclic radical can be substituted one to three times with $C_1$–$C_8$alkyl, $C_1$–$C_8$alkoxy, or halogen, or $R_8$ and $R_9$ stand for —$C(O)R_{10}$, wherein $R_{11}$ can be $C_1$–$C_{25}$-alkyl, $C_5$–$C_{12}$-cycloalkyl, $R_{10}$, —$OR_{12}$ or —$NR_{13}R_{14}$, wherein $R_{12}$, $R_{13}$, and $R_{14}$ stand for $C_1$–$C_{25}$-alkyl, $C_5$–$C_{12}$-cycloalkyl, $C_6$–$C_{24}$-aryl, or
a saturated or unsaturated heterocyclic radical comprising five to seven ring atoms, wherein the ring consists of carbon atoms and one to three hetero atoms selected from the group consisting of nitrogen, oxygen and sulfur, wherein the aryl and heterocyclic radical can be substituted one to three times with $C_1$–$C_8$alkyl or $C_1$–$C_8$alkoxy, or —$NR_8R_9$ stands for a five- or sixmembered heterocyclic radical in which $R_8$ and $R_9$ together stand for tetramethylene, pentamethylene, —$CH_2$—$CH_2$—$O$—$CH_2$—$CH_2$—, or —$CH_2$—$CH_2$—$NR_5$—$CH_2$—$CH_2$—, preferably —$CH_2$—$CH_2$—$O$—$CH_2$—$CH_2$—, and n stands for 0, 1, 2 or 3, and wherein Z stands for a diradical selected from the group consisting of a single bond, $C_2$–$C_6$alkylene, which can be substituted one to three times with $C_1$–$C_4$alkyl, $C_1$–$C_4$alkoxy, or phenyl, phenylene or naphthylene.

Thin film type electroluminescent devices usually consist essentially of a pair of electrodes and at least one charge transporting layer in between. Usually two charge transporting layers, a hole transporting layer (next to the anode) and an electron transporting layer (next to the cathode) are present. Either one of them contains—depending on its properties as hole-transporting or electron-transporting material—an inorganic or organic fluorescence substance as light-emitting material. It is also common, that a light-emitting material is used as an additional layer between the hole-transporting and the electron-transporting layer.

It is presently common to prepare organic electroluminescent ("EL") devices which contain an organic fluorescent substance by a vacuum evaporation process, e.g. described in Appl. Phys. Left., 51, 913 (1987). In general, two types of such vacuum evaporation processes are applied according to the constitution of light emitting material: a one-component type process and a two-components type (or "Host-Guest type" or "binary system") process (e.g. described in J. Appl. Phys., 65, 3610 (1989)).

For emitting a light of red, green or blue color in a one-component system, the light emitting materials themselves have to emit an intense fluorescence of red, green or blue color. Further, a vacuum evaporation process has to give a deposited film of uniform quality, and the film thus formed has to be endowed with appropriate ("carrier") mobility for positive holes and/or electrons i.e. properties of a semiconductor.

Numerous materials emitting light in the green- or blue-colored region are known.

JP-B2 2,749,407 (Pioneer Electron Corp. & Nippon Kayaku Co. Ltd.) describes as a light emitting material N,N'-bis(2,5-di-tert.-butylphenyl)-3,4,9,10-perylenedicarboximide. However, its luminance is as low as 27 cd/m², which is insufficient for commercial applications.

JP-A2 2,296,891 (Ricoh) claims an electroluminescent element comprising a positive electrode, a negative electrode and one organic compound layer or a plurality of organic compound layers held between the positive and negative electrodes, but no hole transporting substance. At least one layer of said organic compound layers is a layer containing a pyrrolopyrrole compound represented by the following formula II

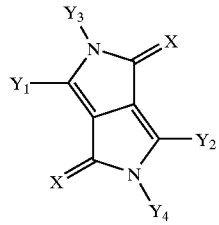

wherein $Y_1$ and $Y_2$ independently from each other represent a substituted or unsubstituted alkyl, cycloalkyl or aryl group, $Y_3$ and $Y_4$ independently represent a hydrogen atom or a substituted or unsubstituted alkyl or aryl group, and X represents an oxygen or a sulfur atom. Only four compounds are mentioned explicitly, namely wherein X stands for oxygen in all cases, and wherein (a) $Y_3$=$Y_4$=methyl and $Y_1$=$Y_2$=p-tolyl, (b) $Y_3$=$Y_4$=methyl and $Y_1$=$Y_2$=hydrogen, (c) $Y_3$=$Y_4$=hydrogen and $Y_1$=$Y_2$=p-tolyl, and (d) $Y_3$=$Y_4$=$Y_1$=hydrogen and $Y_2$=p-chlorophenyl. However, according to JP-A2 5,320,633 (see below), a follow-up study of the same inventors revealed that an emission of light is only observed, if the DPP-compounds II are used together with other compounds. This observation is supported by comparative example 2 of JP-A2 5,320,633, which shows that no emission is observed, if DPP II is used alone, i.e. without the addition of tris(8-hydroxyquinolinato) aluminium ("Alq$_3$").

JP-A2 5,320,633 (Sumitomo) claims an organic EL device having a light emitting layer comprising a light emitting material in an amount of 0.005 to 15 parts by weight of a DPP-compound between a pair of electrodes, wherein at least one electrode being transparent or semi-transparent. Although the main claim is silent about the use of Alq$_3$, it is clear from the specification and the examples, especially from comparative example 2, that Alq$_3$ is an essential feature in the claimed EL element or device.

JP-A2 9003448 (Toyo Ink) claims an organic EL element having between a pair of electrodes a luminous layer containing a DPP-compound as electron-transporting material or an organic compound thin film layer including a luminous layer and an electron-injecting layer wherein the electron-injecting layer contains a DPP compound as the electron-transporting material. In addition, another EL element further comprising a hole-injecting layer is claimed. The disadvantage of the claimed EL devices is that according to the examples always Alq$_3$ and a phenanthrene diamine (as hole-injecting material) have to be used.

EP-A 499,011 claims an organic EL element comprising a DPP compound, however, only systems having no electron-transporting layers are verified. Further, only highly crystalline organic pigments should be employed for a light emitting material. However, one of the requirements for light emitting materials is its morphological stability. Crystalline materials show a tendency to be morphologically modulated in the evaporated film. This becomes a disadvantage for ensuring device durability.

Usually in Host-Guest type light emitting materials, the sensitized fluorescence caused by the Förster type excitation energy transfer from Host to Guest is utilized. Accordingly, in addition to the abovementioned conditions, it is also important for this type of materials to fulfill the condition that the fluorescent spectrum of the Host in the solid state overlaps with the light absorption spectrum of the Guest in the solution state.

As to green-colored light emission, so high an EL emitting efficiency as >10 lm/W is achieved by using Alq$_3$ as Host and a quinacridone derivative as Guest. Such a system is used in practice in monocolor displays.

With regard to blue-colored light emission, Appl. Phys. Lett., 67, 3853 (1995) reports that a high EL emitting efficiency of 1.5 lm/W can be achieved by using a distyryl derivative as Host and an amino-substituted distyryl derivative as Guest. As above, the Guest material is not required to have a high carrier mobility, and therefore not required to be a semiconductor.

Many of the known orange-, red- or yellow-colored fluorescent dyes for use as dyestuff laser have a high fluorescence quantum yield in the solution state. Their Stokes shift, however, is generally small. That is, most of the yellow-, orange- or red-colored fluorescent dyes absorb yellow, orange or red light in the solution state and emit a yellow-, orange- or red-colored fluorescence. Accordingly, if a yellow-, orange- or red-colored fluorescent dye is considered as Guest, the Host material should be a material emitting a yellow-, orange- or red-colored fluorescence in the solid state, as designated by the conditions necessary for realization of a sensitized fluorescence through Förster type excitation energy transfer.

Further, compatibility with the Guest must also be taken into account in addition to the conditions similar to those required of one-component type light emitting materials. In conclusion, the Host material must be a yellow-, orange- to red-colored solid fluorescent material in order to realize a yellow-, orange- or red-colored organic EL luminescence in a two-components system. At the present stage, however, no satisfactory yellow-, orange- or red-light emitting material is known for the same reason as in the one-component system.

EP-A 648770 describes solid fluorescent, soluble latent pigments. However, latent pigments cannot be used for the abovementioned vacuum evaporation processes because they are transformed into insoluble non-fluorescent DPP pigments upon heating.

Hence, the object of this invention was to provide electroluminescent devices emitting yellow, orange or red light, wherein organic light-emitting materials should be used fulfilling intense photoluminescence in the solid state for the one-component system, and/or the Host in the binary system, and in the solution state for the Guest in the binary system, carrier mobility for a positive hole and/or an electron, necessary properties for vacuum evaporation and deposition (such as ability to sublime or evaporate), the ability for a homogeneous film formation, the property of exhibiting a "pure" color, the ability that the electronic potential should match with the electrodes and/or with the substances adjacent to, compatibility of the solid host and the molecular guest in case binary systems are desired, high durability (thermal, electrical etc.) and morphological stability.

Accordingly, the abovementioned electroluminescent devices were found. In addition, a process for its preparation, and new light-emitting materials were found, too.

Typical constitutions of latest organic electroluminescent devices are:

(i) an anode/a hole transporting layer/an electron transporting layer/a cathode, in which compounds I are used either as positive-hole transport compounds, which is exploited to form the light emitting and hole transporting layers, or as electron transport compounds, which can be exploited to form the light-emitting and electron transporting layers, and (ii) an anode/a hole transporting layer/a light-emitting layer/an electron transporting layer/a cathode, in which the compounds I form the light-emitting layer regardless of whether they exhibit positive-hole or electron transport properties in this constitution.

It is possible that the light-emitting layer can consist of two or more fluorescent substances of formula I for energy donor(s) and/or energy acceptor(s).

The devices can be prepared in several ways. Usually, vacuum evaporation is extensively used for the preparation. Preferably, the organic layers are laminated in the above order on a commercially available indium-tin-oxide ("ITO") glass substrate held at room temperature, which works as the anode in the constitutions. The membrane thickness is preferably in the range of 1 to 10,000 nm, more preferably 1 to 5,000 nm, more preferably 1 to 1,000 nm, more preferably 1 to 500 nm. The cathode metal such as Mg/Ag alloy and Li—Al binary system of ca. 200 nm is laminated on the top of the organic layers. The vacuum during the deposition is preferably less than 0.1333 Pa ($1\times10^{-3}$ Torr), more preferably less than $1.333\times10^{-3}$ Pa ($1\times10^{-5}$ Torr), more preferably less than $1.333\times10^{-4}$ Pa ($1\times10^{-6}$ Torr).

As anode usual anode materials which possess high work function such as metals like gold, silver, copper, aluminum, indium, iron, zinc, tin, chromium, titanium, vanadium, cobalt, nickel, lead, manganese, tungsten and the like, metallic alloys such as magnesium/copper, magnesium/silver, magnesium/aluminum, aluminum/indium and the like, semiconductors such as Si, Ge, GaAs and the like, metallic oxides such as indium-tin-oxide ("ITO"), ZnO and the like, metallic compounds such as CuI and the like, and furthermore, electroconducting polymers such polyacetylene, polyaniline, polythiophene, polypyrrole, polyparaphenylene and the like, preferably ITO, most preferably ITO on glass as substrate can be used. Of these electrode materials, metals, metallic alloys, metallic oxides and metallic compounds can be transformed into electrodes, for example, by means of the sputtering method. In the case of using a metal or a metallic alloy as a material for an electrode, the electrode can be formed also by the vacuum deposition method. In the case of using a metal or a metallic alloy as a material forming an electrode, the electrode can be formed, furthermore, by the chemical plating method (see for example, Handbook of Electrochemistry, pp 383–387, Mazuren, 1985). In the case of using an electroconducting polymer, an electrode can be made by forming it into a film by means of anodic oxidation polymerization method onto a substrate which is previously provided with an electroconducting coating. The thickness of an electrode to be formed on a substrate is not limited to a particular value, but, when the substrate is used as a light emitting plane, the thickness of the electrode is preferably within the range of from 1 nm to 100 nm, more preferably, within the range of from 5 to 50 nm so as to ensure transparency.

In a preferred embodiment ITO is used on a substrate having an ITO film thickness in the range of from 10 nm (100 Å) to 1$\mu$ (10000 Å), preferably from 20 nm (200 Å) to 500 nm (5000 Å). Generally, the sheet resistance of the ITO film is chosen in the range of not more than 100 $\Omega/cm^2$, preferred from not more than 50 $\Omega/cm^2$.

Such anodes are commercially available from e.g. Japanese manufacturers such as Geomatech Co. Ltd., Sanyo Vacuum Co. Ltd., Nippon Sheet Glass Co. Ltd.

As substrate either an electronconducting or electrically insulating material can be used. In case of using an electroconducting substrate, a light emitting layer or a positive hole transporting layer is directly formed thereupon, while in case of using an electrically insulating substrate, an electrode is firstly formed thereupon and then a light emitting layer or a positive hole transporting layer is superposed.

The substrate may be either transparent, semi-transparent or opaque. However, in case of using a substrate as an indicating plane, the substrate must be transparent or semi-transparent.

Transparent electrically insulating substrates are, for example, inorganic compounds such as glass, quartz and the like, organic polymeric compounds such as polyethylene, polypropylene, polymethylmethacrylate, polyacrylonitrile, polyester, polycarbonate, polyvinylchloride, polyvinylalcohol, polyvinylacetate and the like. Each of these substrates can be transformed into a transparent electroconducting substrate by providing it with an electrode according to one of the methods described above.

As examples of semi-transparent electrically insulating substrates, there are inorganic compounds such as alumina; YSZ (yttrium stabilized zirconia) and the like, organic polymeric compounds such as polyethylene, polypropylene, polystyrene, epoxy resin and the like. Each of these substrates can be transformed into a semi-transparent electroconducting substrate by providing it with an electrode according to one of the abovementioned methods.

As examples of opaque electroconducting substrates, there are metals such as aluminum, indium, iron, nickel, zinc, tin, chromium, titanium, copper, silver, gold, platinum and the like, various elctroplated metals, metallic alloys such as bronze, stainless steel and the like, semiconductors such as Si, Ge, GaAs, and the like, electroconducting polymers such as polyaniline, polythiophene, polypyrrole, polyacetylene, polyparaphenylene and the like.

A substrate can be obtained by forming one of the above listed substrate materials to a desired dimension. It is preferred that the substrate has a smooth surface. Even if it has a rough surface, however, it will not cause any problem for practical use, provided that it has round unevenness having a curvature of not less than 20 $\mu$m. As for the thickness of the substrate, there is no restriction as far as it ensures sufficient mechanical strength. As cathode usual cathode materials which possess low work function such as alkali metals, earth alkaline metals, group 13 elements, silver, and copper as well as alloys or mixtures thereof such as sodium, lithium, potassium, sodium-potassium alloy, magnesium, magnesium-silver alloy, magnesium-copper alloy, magnesium-aluminum alloy, magnesium-indium alloy, aluminum, aluminum-aluminum oxide alloy, aluminum-lithium alloy, indium, calcium, and materials exemplified in EP-A 499,011 such as electroconducting polymers e.g. polypyrrole, polythiophene, polyaniline, polyacetylene etc., preferably Mg/Ag alloys, or Li—Al compositions can be used.

In a preferred embodiment magnesium-silver alloy or a mixture of magnesium and silver mixture, or lithium-aluminum alloy or a mixture of lithium and aluminum can be used in a film thickness in the range of from 10 nm (100 Å) to 1 $\mu$m (10000 Å), preferably from 20 nm (200 Å) to 500 nm (5000 Å).

Such cathodes can be deposited on the foregoing electron transporting layer by known vacuum deposition techniques described above.

In a preferred ambodiment of this invention a light-emitting layer can be used between the hole transporting layer and the electron transporting layer. Usually it is prepared by forming a thin film of a DPP compound of formula I on the hole transporting layer.

As methods for forming said thin film, there are, for example, the vacuum deposition method, the spin-coating method, the casting method, th Langmuir-Blodgett ("LB") method and the like. Among these methods, the vacuum deposition method, the spin-coating method and the casting method are particularly preferred in view of ease in operation and cost.

In case of forming a thin film using a DPP compound I by means of the vacuum deposition method, the conditions under which the vacuum deposition is carried out are usually strongly dependent on the properties, shape and crystalline state of the compound. However, optimum conditions can be selected for example within the range of from 100 to 400° C. in temperature for the heating boat, −100 to 350° C. in substrate temperature, $1.33 \times 10^4$ Pa ($1 \times 10^2$ Torr) to $1.33 \times 10^{-4}$ Pa ($1 \times 10^{-6}$ Torr) in pressure and 1 pm to 6 nm/sec in deposition rate.

In an organic EL element, the thickness of the light emitting layer thereof is one of the factors determining its light emission properties. For example, if a light emitting layer is not sufficiently thick, a short circuit can occur quite easily between two electrodes sandwiching said light emitting layer, and therefor, no EL emission is obtained. On the other hand, if the light emitting layer is excessively thick, a large potential drop occurs inside the light emitting layer because of its high electrical resistance, so that the threshold voltage for EL emission increases. Accordingly, it is necessary to limit the thickness of an organic light emitting layer within the range of from 5 nm to 5 $\mu$m. A preferable thickness is within the range of from 10 nm to 500 nm.

In the case of forming a light emitting layer by using the spin-coating method and the casting method, the coating can be carried out using a solution prepared by dissolving the DPP I in a concentration of from 0.0001 to 90% by weight in an appropriate organic solvent such as benzene, toluene, xylene, tetrahydrofurane, methyltetrahydrofurane, N,N-dimethylformamide, dichloromethane, dimethylsulfoxide and the like. Herein, the higher the concentration of DPP I, the thicker the resulting film, while the lower the concentration, the thinner the resulting film. However, if the concentration exceeds 90% by weight, the solution usually is so viscous that it no longer permits forming a smooth and homogenous film. On the other hand, as a rule, if the concentration is less than 0.0001% by weight, the efficiency of forming a film is too low to be economical. Accordingly, a preferred concentration of DPP I is within the range of from 0.01 to 80% by weight.

In the case of using the above spin-coating or casting method, it is possible to further improve the homogeneity and mechanical strength of the resulting layer by adding a polymer binder in the solution for forming the light emitting layer. In principle, any polymer binder may be used, provided that it is soluble in a solvent in which DPP I is dissolved. Examples of such polymer binders are polycarbonate, polyvinylalcohol, polymethacrylate, polymethylmethacrylate, polyester, polyvinylacetate, epoxy resin and the like. A solution for forming a light emitting layer may have any concentrations of DPP I, of a polymer binder and solvent. However, if the solid content composed of the polymer binder and DPP I exceeds 99% by weight, the fluidity of the solution is usually so low that it is impossible to form a light emitting layer excellent in homogeneity. On the other hand, if the content of DPP I is substantially smaller than that of the polymer binder, in general the electrical resistance of said layer is very large, so that it does not emit light unless a high voltage is applied thereto. Furthermore, since the concentration of DPP I in the layer is small in this case, its light emission efficiency is relatively low. Accordingly, the preferred composition ratio of a polymer binder to DPP I is chosen within the range of from 10:1 to 1:50 by weight, and the solid content composed of both components in the solution is preferably within the range of from 0.01 to 80% by weight, and more preferably, within the range of about 0.1 to 60% by weight.

In the case of forming a light emitting layer by the spin-coating method or casting method, the thickness of said layer may be selected in the same manner as in the case of forming a light emitting layer by the vacuum deposition method. That is, the thickness of the layer preferably is chosen within the range of from 5 nm to 5 μm, and more preferably, within the range of from 10 nm to 500 nm.

As hole-transporting layers known organic hole transporting compounds such as polyvinyl carbazole,

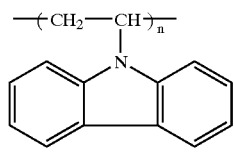

a TPD compound disclosed in J. Amer. Chem. Soc. 90 (1968) 3925

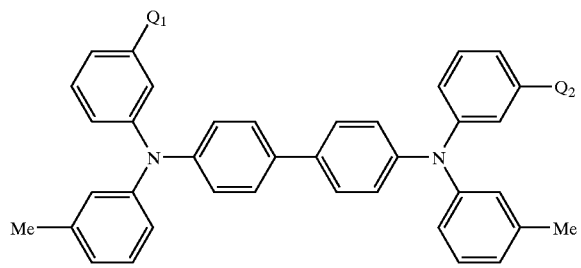

wherein $Q_1$ and $Q_2$ each represent a hydrogen atom or a methyl group;

a compound disclosed in J. Appl. Phys. 65(9) (1989) 3610

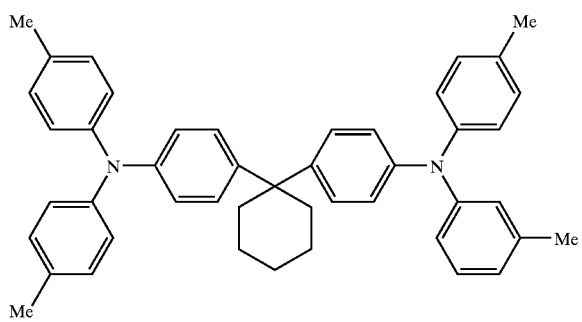

a stilbene based compound

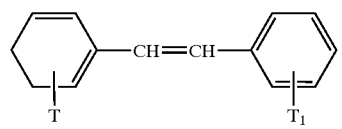

wherein T and $T_1$ stand for an organic rest a hydrazone based compound

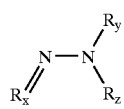

and the like.

Compounds to be used as a positive hole transporting material are not restricted to the above listed compounds. Any compound having a property of transporting positive holes can be used as a positive hole transporting material such as triazole derivatives, oxadiazole derivatives, imidazole derivatives, polyarylalkane derivatives, pyrazoline derivative, pyrazolone derivatives, phenylene diamine derivatives, arylamine derivatives, amino substituted chalcone derivatives, oxazole derivatives, stilbenylanthracene derivatives, fluorenone derivatives, hydrazone derivatives, stilbene derivatives, copolymers of aniline derivatives, electro-conductive oligomers, particularly thiophene oligomers, porphyrin compounds, aromatic tertiary amine compounds, stilbenyl amine compounds etc. Particularly, aromatic tertiary amine compounds such as N,N,N',N'-tetraphenyl-4,4'-diaminobiphenyl, N,N'-diphenyl-N,N'-bis(3-methylphenyl)-4,4'-diaminobiphenyl (TPD), 2,2'-bis(di-p-torylaminophenyl)propane, 1,1'-bis(4-di-torylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quaterphenyl, N,N,N-tri(p-tolyl)amine, 4-(di-p-tolylamino)-4'-[4-(di-p-tolylamino)stilyl]stilbene, 4-N,N-diphenylamino-(2-diphenylvinyl)benzene, 3-methoxy-4'-N,N-diphenylaminostilbene, N-phenylcarbazole etc.

Furthermore, 4,4'-bis[N-(1-naphthyl)-N-phenylamino]biphenyl disclosed in U.S. Pat. No. 5,061,569, the compounds in which three triphenylamine units are bound to a nitrogen atom like "star-burst" structure e.g. 4,4',4"-tris[N-(3-methylphenyl)-N-phenylamino]triphenylamine disclosed in EP-A 508,562.

A positive hole transporting layer can be formed by preparing an organic film containing at least one positive hole transporting material on the anode. The positive hole transporting layer can be formed by the vacuum deposition method, the spin-coating method, the casting method, the LB method and the like. Of these methods, the vacuum deposition method, the spin-coating method and the casting method are particularly preferred in view of ease and cost.

In the case of using the vacuum deposition method, the conditions for deposition may be chosen in the same manner as described for the formation of a light emitting layer (see above). If it is desired to form a positive hole transporting layer comprising more than one positive hole transporting material, the coevaporation method can be employed using the desired compounds.

In the case of forming a positive hole transporting layer by the spin-coating method or the casting method, the layer can be formed under the conditions described for the formation of the light emitting layer (see above).

As in the case of forming a light emitting layer using a solution containing a polymer binder, a smoother and more homogeneous positive hole transporting layer can be formed by using a solution containing a binder and at least one positive hole transporting material. The coating using such a solution can be performed in the same manner as in cases of forming a light emitting layer using a polymer binder. Any polymer binder may be used, provided that it is soluble in a solvent in which at least one positive hole transporting material is dissolved. Examples of appropriate polymer binders and of appropriate and preferred concentrations are given above when describing the formation of a light emitting layer.

The thickness of a positive hole transporting layer is preferably chosen in the range of from 0.5 to 1000 nm, preferably from 1 to 100 nm, more preferably from 2 to 50 nm.

As electron transporting materials for an electron-transporting layer it is preferred to have a high electron injection efficiency from the cathode and a high electron mobility. The following materials can be exemplified for electron transporting materials: tris(8-hydroxyquinolinato)aluminum(III) and its derivatives, bis(10-hydroxybenzo[h]quinolinato) beryllium(II) and its derivatives, oxadiazole derivatives such as 2-(4-biphenyl)-5-(4-tert.-butylphenyl)-1,3,4-oxadiazole and its dimer systems such as 1,3-bis(4-tert.-butylphenyl-1, 3,4)oxadiazolyl)biphenylene and 1,3-bis(4-tert.-butylphenyl-1,3,4-oxadiazolyl)phenylene, triazole derivatives, phenanthroline derivatives or perylene tetracarboxylic acid derivatives such as disclosed in Appl. Phys. Lett. 48 (2) (1986) 183.

An electron transporting layer can be formed by preparing an organic film containing at least one electron transporting material on the hole transporting layer or on the light-emitting layer. The electron transporting layer can be formed by the vacuum deposition method, the spin-coating method, the casting method, the LB method and the like.

As in the case of forming a light emitting layer or a positive hole transporting layer by using a solution containing a polymer binder, a smoother and more homogeneous electron transporting layer can be formed by using a solution containing a binder and at least one electron transporting material.

The thickness of an electron transporting layer is preferably chosen in the range of from 0.5 to 1000 nm, preferably from 1 to 100 nm, more preferably from 2 to 50 nm.

Yellow to red fluorescent light-emitting compounds means that the used light-emitting compounds preferably have a fluorescence emission maximum in the range of from 500 to 780, more preferably from 520 to 750, more preferred from 540 to 700 nm. Further, the inventive compounds preferably exhibit an absorption maximum in the range of 450 to 580 nm.

The light-emitting compounds I usually exhibit a fluorescence quantum yield ("FQY") in the range of from $1 > FQY \geq 0.3$ (measured in aerated toluene or DMF). Further, in general, the inventive compounds I exhibit a molar absorption coefficient in the range of from 5000 to 100000.

A preferred embodiment relates to DPP-compounds I, wherein $R_1=R_2$, and $Ar_1=Ar_2$, particularly preferred wherein in addition to the above $R_3=R_4=H$, m=0 and n=0, most preferred are DPP-compounds in which (a) $R_1=R_2=C_1-C_8$alkyl, $Ar_1=Ar_2$=phenyl or stilbene, $R_7=-NR_8R_9$ in 4-position, $R_5=R_6$=hydrogen, and $R_8=R_9=C_1-C_8$alkyl or phenyl, or (b) $R_1=R_2=C_1-C_8$alkyl, $-(CH_2)_m$-Ph, $Ar_1=Ar_2$=phenyl or stilbene, $R_5=R_6$=hydrogen, $R_7=-SR_7$, $-OR_{10}$, $-N(R_8)_2$ or unsubstituted or substituted phenyl in para-position, and $R_8=C_1-C_8$alkyl, phenyl or a heterocyclic radical, both unsubstituted or substituted, or $C_5-C_{12}$-cycloalkyl, or (c) $R_1=R_2=-CH_2$-Ph, wherein phenyl can be substituted with phenyl, naphthyl or $C_1-C_4$alkyl up to two times, $Ar_1=Ar_2$=phenyl or 1- or 2-naphthyl, $R_5=R_6$=hydrogen, $R_7$=hydrogen or $-OMe$, in case where $Ar_1=Ar_2=1$- or 2-naphthyl, or, in all other cases, $C_1-C_8$alkyl or phenyl.

Particularly preferred DPP-compounds I are the following compounds:

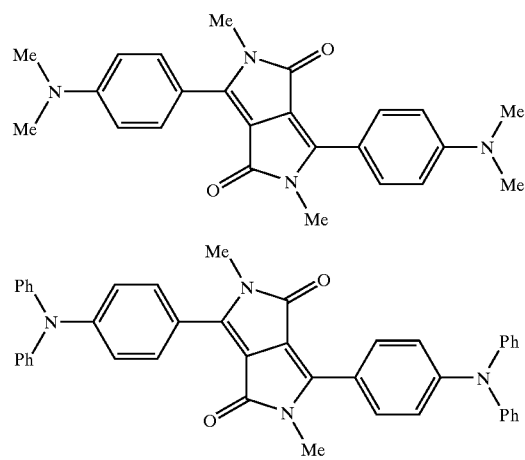
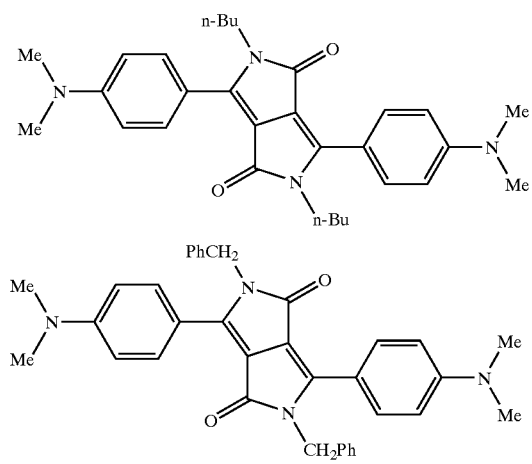

-continued
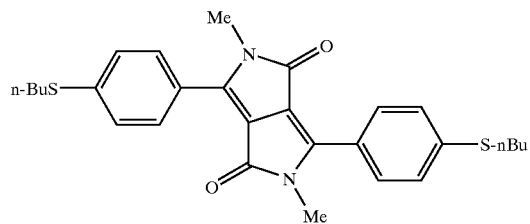
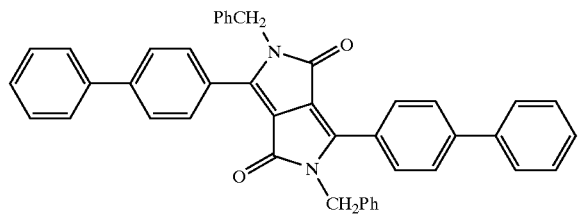
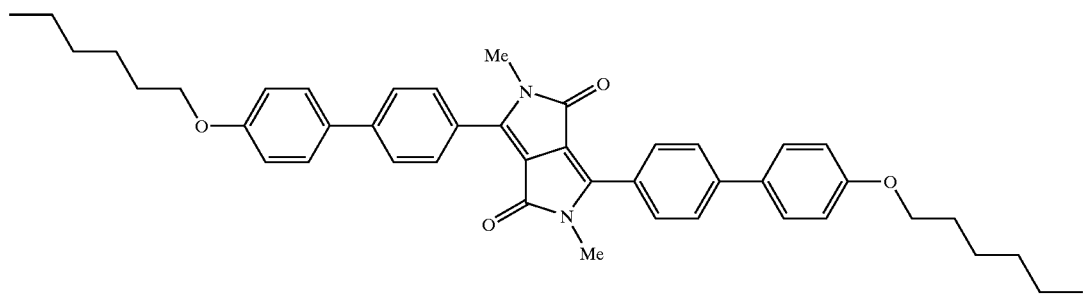
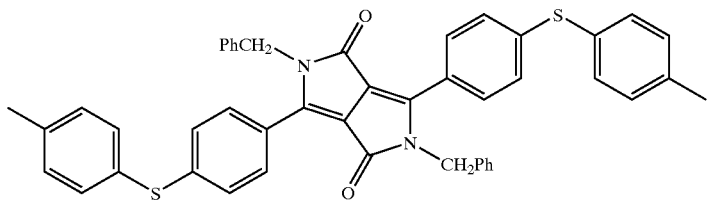
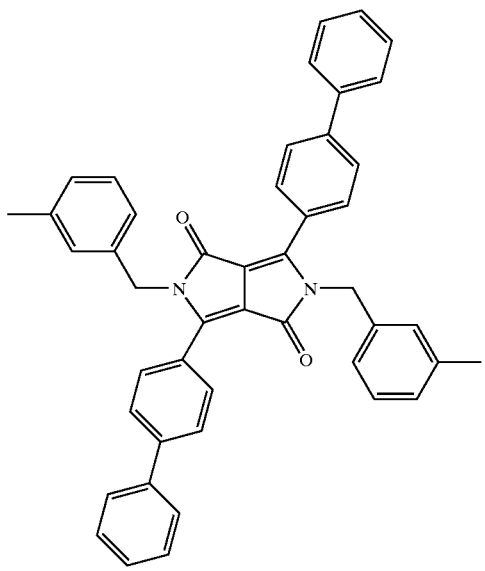
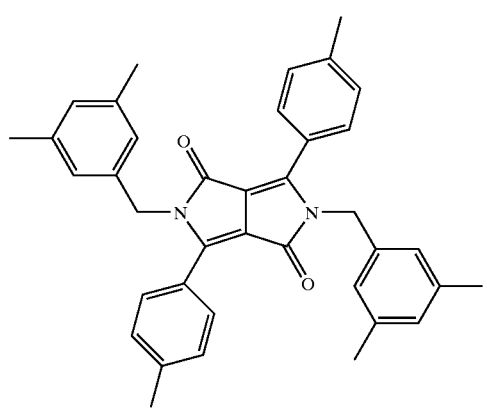

-continued
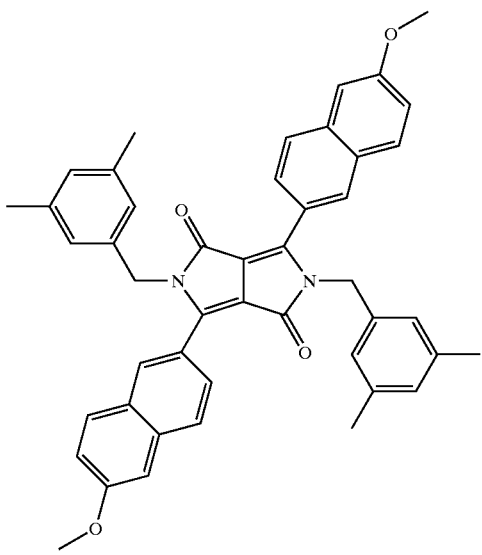
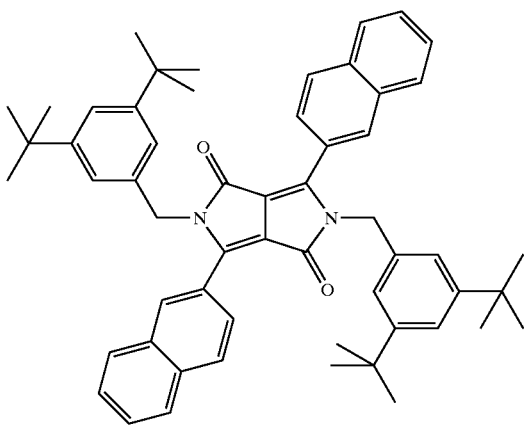
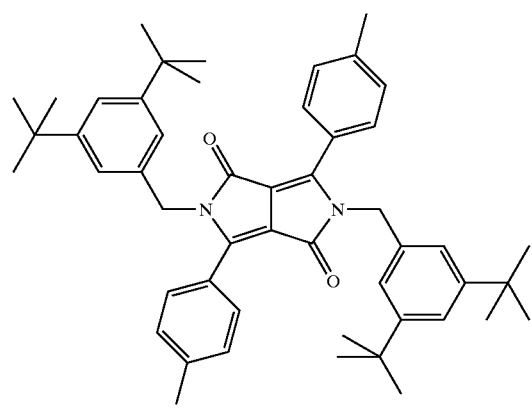
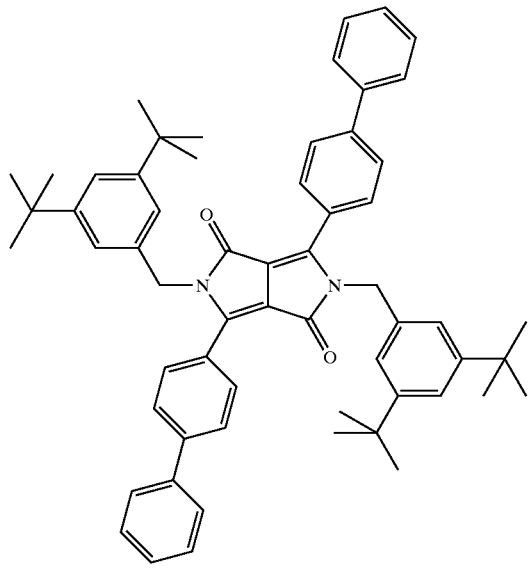
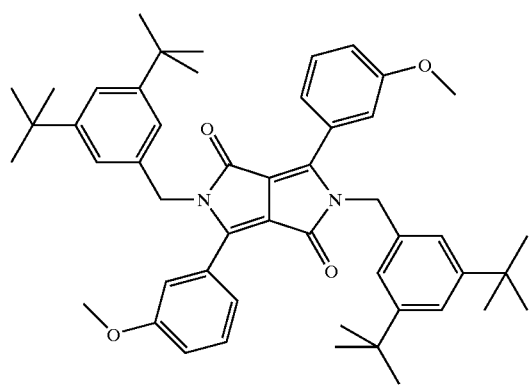
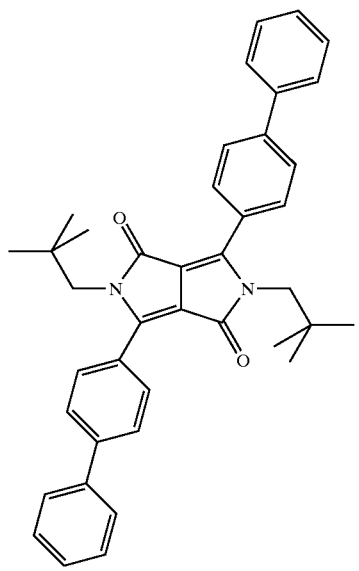

-continued
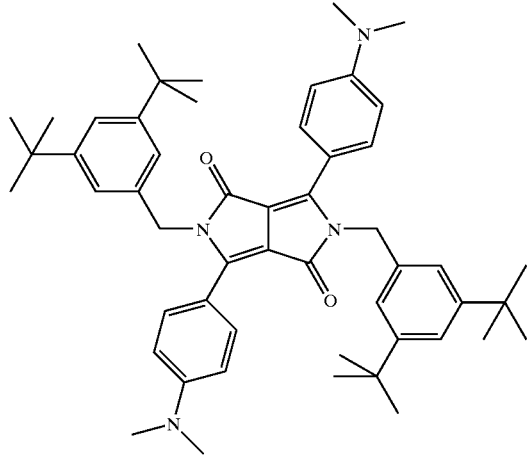
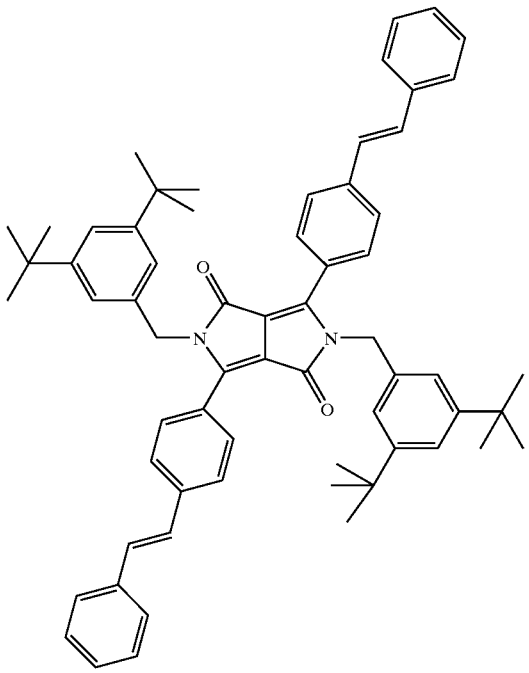
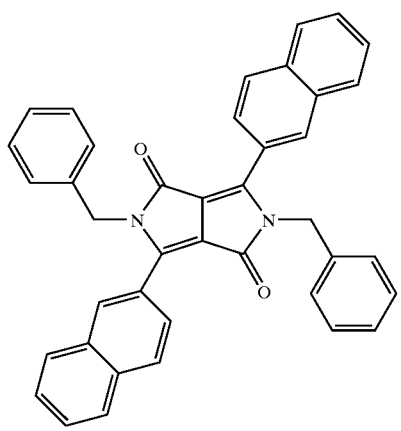
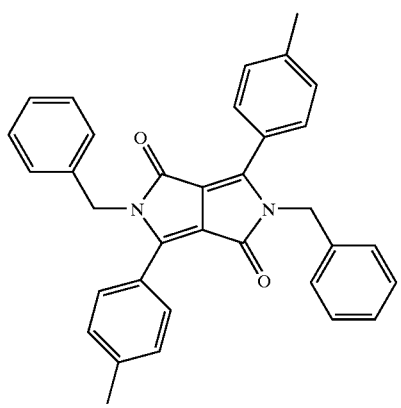
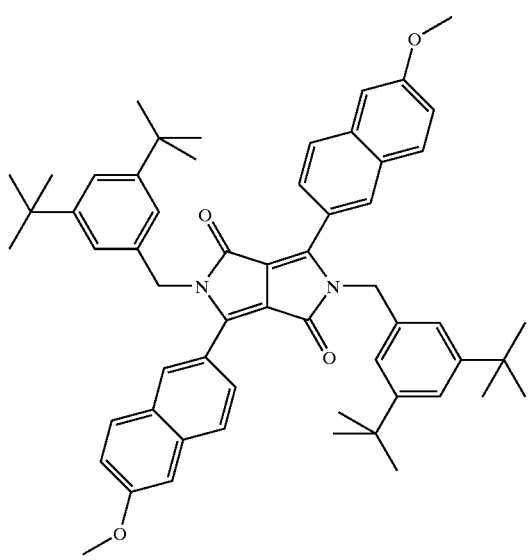
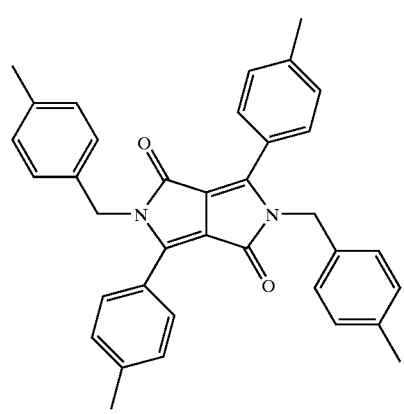

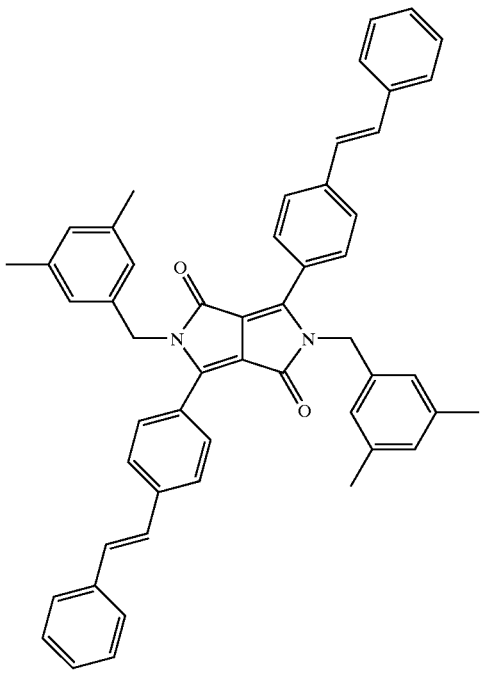

$C_1$–$C_{25}$alkyl is typically linear or branched—where possible—methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl, octadecyl, eicosyl, heneicosyl, docosyl, tetracosyl or pentacosyl, preferably $C_1$–$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl, more preferably $C_1$–$C_4$alkyl such as typically methyl, ethyl, n-propyl, isopropyl, n-butyl, sec.-butyl, isobutyl, tert.-butyl; $C_1$–$C_6$alkyl stands for methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl; $C_1$–$C_3$alkyl stands for methyl, ethyl, n-propyl, or isopropyl.

$C_1$–$C_8$alkoxy is typically methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$–$C_4$alkoxy such as typically methoxy, ethoxy, n-propoxy, isopropoxy, n-butoxy, sec.-butoxy, isobutoxy, tert.-butoxy.

$C_6$–$C_{24}$aryl is typically phenyl, 1-naphthyl, 2-naphthyl, 4-biphenyl, phenanthryl, 2- or 9-fluorenyl or anthracenyl, preferably $C_6$–$C_{12}$aryl such as phenyl, 1-naphthyl, 2-naphthyl, 4-biphenyl.

$C_7$–$C_{24}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$–$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$–$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl.

$C_5$–$C_{12}$cycloalkyl is typically cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, cyclooctyl.

Heteroaryl with five to seven ring atoms, wherein nitrogen, oxygen or sulfur are the possible hetero atoms, is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the abovementioned mono- or bicyclic heterocyclic radicals.

The inventive DPP-compounds I can be synthesized according to methods well known in the art such as described in EP-A 133,156, e.g. in analogy to example 15.

A preferred embodiment of this invention relates to a process for the preparation of the inventive compounds I or III by treating in a first step the DPP derivative of formula Va or Vb

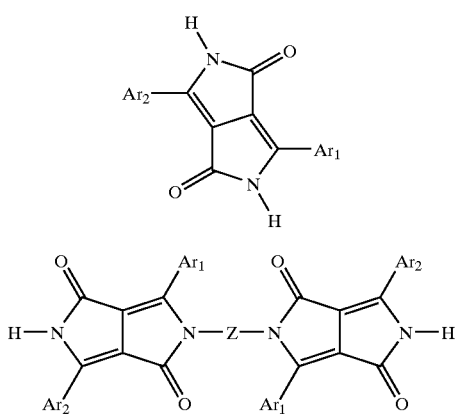

Va

Vb with a base, then, in a second step, treating the reaction mixture obtained in the first step with a usual alkylating agent, wherein in the first step the base is a hydride, an alkali metal alkoxide or a carbonate, and the alkylating agent is a sulfonate, tosylate, mesylate, carbonate, sulfate, or halogen compound of the formula $(R_1)_{1\ or\ 2}X$, wherein X stands for $SO_3$—, (p-Me-phenyl)$SO_2$—, (2,4,6-trimethyl-phenyl)$SO_2$—, —$CO_3$—, —$SO_4$—, or halogen such as chlorine, bromine or iodine, preferably chlorine, bromine or iodine, particularly preferred for bromine or iodine, or a mixture of $(R_1)_{1\ or\ 2}X$ and $(R_2)_{1\ or\ 2}X$.

As a hydride usually an alkali metal hydride such as sodium hydride, lithium hydride, or potassium hydride, as an alkali metal alkoxide in general an alkali metal $C_1$–$C_4$alkoxide such as sodium or potassium tert. butoxide, sodium tert.-amylate, and as a carbonate usually sodium or potassium carbonate can be used, preferably sodium hydride.

Usually, the first step of the preferred preparation of compound I or III starting from compound Va, resp. Vb, is carried out at a temperature in the range of from −25 to 100, preferably from 0 to 25° C.

Preferably, the reaction is carried out in the presence of a solvent, preferably a dipolar aprotic solvent such as carboxamides, lactams, urea derivatives, sulfones and nitrobenzene such as dimethyl formamide ("DMF"), dimethyl acetamide ("DMA"), N-methylpyrrolidone ("NMP"), N,N'-dimethylethylene urea and N,N'-dimethylpropylene urea.

In case a solvent is used, a weight ratio of solvent to DPP-compound is chosen in the range of from 100:1 to 5:1, preferably from 25:1 to 10:1.

In addition, it is preferred to carry out the first step in the presence of a phase transfer catalyst such as a tetra alkyl ammonium halide such as tetraethyl ammonium bromide.

Usually, a molar ratio of base to DPP-compound Va, resp. Vb, is chosen in the range of from 10:1 to 2:1, preferably from 4:1 to 2:1.

Preferably, a molar ratio of DPP-compound Va, resp. Vb, to the phase transfer catalyst is chosen in the range of from 100:1 to 5:1, preferably from 25:1 to 10:1.

Generally, the reaction time depends inter alia on the reactivity of the chosen reactants and the chosen temperature. As an example, if room temperature is chosen as reaction temperature, a reaction time is as a rule in the range of from 0.5 to 24 hours.

Preferably, the halogen compound $R_1$—X (or the aforementioned mixture) is added to the reaction mixture obtained in the first step in the same solvent used in the first step.

The reaction temperature in the second process step usually is chosen in the range of from 0 to 160, preferably from 25 to 110° C., depending on inter alia the desired reaction pressure and solvent used.

The reaction time generally is chosen in the range of from 0.5 to 120, preferably from 12 to 60 hours.

As a rule the molar ratio of $R_1$—X to DPP compound Va, resp. Vb, is chosen in the range of from 10:1 to 2:1, preferably from 4:1 to 2:1.

In case a solvent is used, the amount of solvent usually is chosen in the range of from 100:1 to 5:1, preferably from 25:1 to 10:1, based on the amount of halogen compound $R_1$—X. Further, preferably the same solvent is used as in the first step, if a solvent is used in the first step. If no solvent is used in the first step, the same solvents can be used as mentioned above.

The obtained reaction mixture can be worked up by applying methods well known in the art, e.g. by precipitating the product in the presence of an appropriate solvent such as water, and, if deemed necessary, by re-crystallization in an appropriate solvent such as ethanol. Other methods for example are the addition of an alcohol to quench the excess base followed by filtration.

Compounds Va are described e.g. in U.S. Pat. No. 4,579,949, and/or can be prepared according to the method described therein, in which an appropriate nitrile is reacted with a corresponding dialkyl or diaryl succinate, e.g. $NC$—$Ar_1$ is reacted with sodium tert.-amyl alcohol followed by the addition of diisopropyl succinate. This method is preferred in case $Ar_1$ and/or $Ar_2$ stand for a biphenyl radical (i.e. $R_5$ and/or $R_6$ stand for phenyl or substituted phenyl in 4-position), or for the compounds described below (DPP VIa).

Compounds Vb can be prepared e.g. via the following route

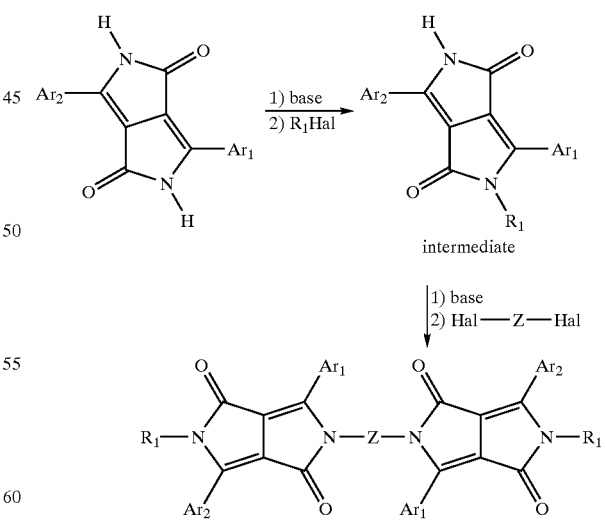

Of course, instead of using $R_1$Hal, a mixture of $R_1$-Hal and $R_2$-Hal can be used which then would lead to the general formula Vb. Usually, $R_1$Hal, resp. the mixture of $R_1$ Hal and $R_2$Hal, is used in a molar amount in the range of from 0.4–0.6:1, related to the starting DPP derivative. Accordingly, generally the molar amount of Hal-Z-Hal/intermediate is chosen in the range of from 0.4–0.6:1.

Compounds I, resp. III, are also available in analogy to the method described in EP-A 353,184, which comprises reacting a DPP-compound of formula VIa or VIb

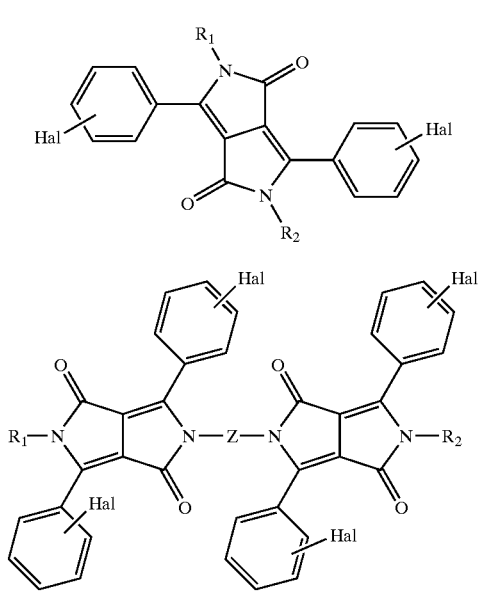

wherein Hal stands for halogen such as fluorine, chlorine, bromine or iodine, preferably chlorine or bromine, with a nucleophilic agent such as a secondary amine, $HNR_8R_9$, a thiol, $HSR_8$, or $HS(O)_nR_8$, an alcohol, $HOR_{10}$, a diselenide, $R_8(O)_nSe—Se(O)_nR_8$, preferably in a molar ratio of DPP VIa, resp. VIb:nucleophilic agent in the range of 1.2:1 to 0.8:1, or, if $R_2$ has the same meaning as $R_1$ in the range of from 1:2.5 to 1:1, in the presence of an anhydrous dipolar aprotic solvent, and of an anhydrous base in an amount in the range of from usually 0.1 to 15 moles per mole of the nucleophilic agent, at a temperature in the range of from usually 100 to 220° C. and under a pressure generally in the range of from 100 to 300 kPa.

Examples of suitable anhydrous dipolar aprotic solvents are carboxamides, lactams, urea derivatives, sulfones and nitrobenzene such as DMF, DMA, NMP, N,N'-dimethylethylene urea and N,N'-dimethylpropylene urea.

Suitable anhydrous bases are e.g. anhydrous organic bases such as quinoline, or preferably, an excess of the secondary amine used for the amination, the aforementioned carbonates such as sodium or potassium carbonate and alkali metal hydrides such as sodium hydride. In case a diselenide, $R_7(O)_nSe—Se(O)_nR_7$, is used, an alkali metal hydride, preferably sodium hydride, has to be used as a base.

The corresponding 1- and 2-naphthyl-derivatives can be prepared analogously.

DPP-compounds VIa and VIb are known and/or can be prepared e.g. according to the method described in U.S. Pat. No. 4,579,949, which methods comprises reacting a dialkyl or diaryl succinate with a nitrile, e.g. dimethyl succinate can be reacted with p-chloro benzonitrile according to example 6 in U.S. Pat. No. 4,579,949 to yield the corresponding DPP compound VIa, in which Hal stands for chlorine.

Compounds $R_1$—X are commercially available or can be prepared by methods well known in the art.

A further embodiment of the invention on hand concerns a process for the preparation of the inventive compounds I resp. III (a) in treating in a first step the DPP derivative of formula VIa, resp. VIb, with a nucleophilic agent such as a secondary amine, $HNR_8R_9$, a thiol, $HSR_8$, or $HS(O)_nR_8$, an alcohol, $HOR_{10}$, a diselenide, $R_8(O)_nSe—Se(O)_nR_8$, preferably in a molar ratio of DPP VIa, resp. VIb:nucleophilic agent in the range of 1.2:1 to 0.8:1, or, if $R_2$ has the same meaning as $R_1$ in the range of from 1:2.5 to 1:1, in the presence of an anhydrous dipolar aprotic solvent, and of an anhydrous base in an amount in the range of from usually 0.1 to 15 moles per mole of the nucleophilic agent, at a temperature in the range of from usually 100 to 220° C. and under a pressure generally in the range of from 100 to 300 kPa, and optionally isolating the obtained compound V, (b) then treating the obtained compound Va, resp. Vb, with a base, thereafter in a second step, treating the reaction mixture obtained in the first step of (b) with an usual alkylating agent, wherein in the first step of (b) the base is a hydride, an alkali metal alkoxide or a carbonate, and the alkylating agent is a sulfonate, tosylate, mesylate, carbonate, sulfate, or halogen compound of the formula $(R_1)_{1\ or\ 2}X$, wherein X stands for $SO_3$—, (p-Me-phenyl)$SO_2$—, (2,4,6-trimethyl-phenyl)$SO_2$—, —$CO_3$—, —$SO_4$—, or halogen, or a mixture of $(R_1)_{1\ or\ 2}X$ and $(R_2)_{1\ or\ 2}X$ (it is evident, that the number of $R_1$-units (either one or two) in $(R_1)_{1\ or\ 2}X$ depends on the nature of the chosen rest X, i.e. there can be only two $R_1$-units if X stands for a divalent anion such as —$CO_3$—, —$SO_4$— etc.).

Water-soluble compounds I, resp. III, i.e. inventive compounds I or III being substituted with a functional group capable of increasing the solubility in water such as a tertiary amino group, $SO_3^-$, or $PO_4^{2-}$, can be prepared by using well-known methods in the art. The following routes are representative examples, and, hence, do not restrict the invention just to these examples:

DPP compound V $\xrightarrow[\text{2) Br—(CH}_2)_r\text{—Br}]{\text{1) NaH/NMP}}$

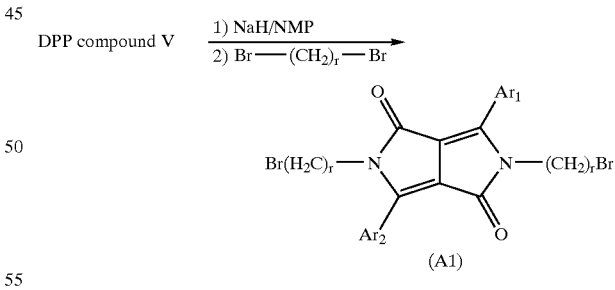

wherein r stands for an integer from usually 2 to 25; instead of linear alkyl groups, one could also use branched alkyl groups or aralkyl groups such as Br—$(CH_2)_{r1}$-aryl-$(CH_2)_{r2}$—Br, $r_1$ and $r_2$ usually being whole numbers in the range of from 0 to 10;

A1 $\xrightarrow[\text{2) conc. HBr, heat}]{\text{1) P(OR)}_3}$

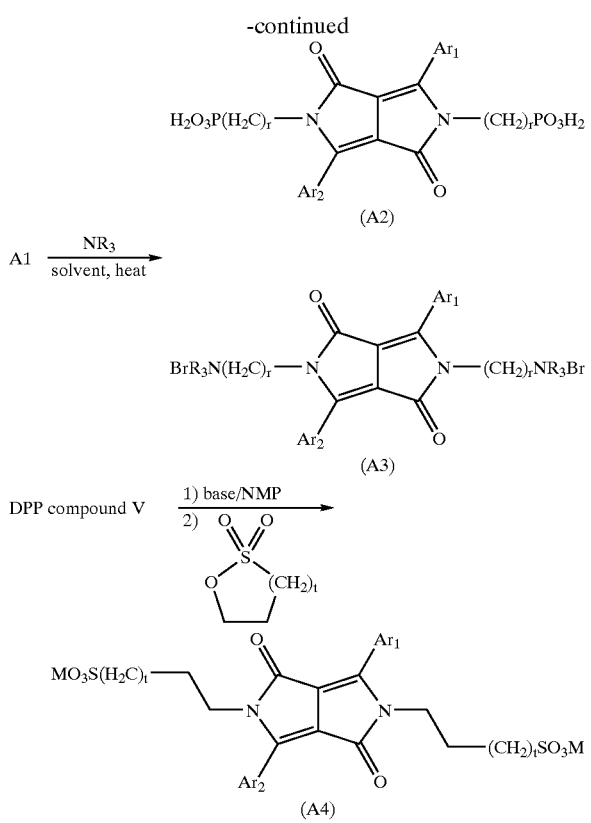

wherein M stands for a metal ion such as sodium or potassium, and t is 1 or 2

Accordingly, corresponding compounds III are available via such route.

Another embodiment of the present invention is related to a method of coloring high molecular weight organic materials (having a molecular weight usually in the range of from $10^3$ to $10^7$ g/mol) by incorporating the inventive fluorescent DPP compounds I or III by known methods in the art.

As high molecular weight organic materials the following can be used such as biopolymers, and plastic materials, including fibres.

The present invention relates preferably to the use of the inventive DPPs I or III for the preparation of inks, for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of colorants, for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of color filters, especially for visible light in the range from 400 to 700 nm, for liquid-crystal displays (LCDs) or charge combined devices (CCDs) or for the preparation of cosmetics or for the preparation of polymeric ink particles, toners, dry copy toners liquid copy toners, or electrophotographic toners.

Illustrative examples of suitable organic materials of high molecular weight which can be colored with the inventive fluorescent DPPs I or III of this invention are vinyl polymers, for example polystyrene, poly-α-methylstyrene, poly-p-methylstyrene, poly-p-hydroxystyrene, poly-p-hydroxyphenylstyrene, polymethyl methacrylate and polyacrylamide as well as the corresponding methacrylic compounds, polymethylmaleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers which are derived from maleinimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylene sulfides; polyepoxides; polyolefins such as polyethylene and polypropylene; polyalkadienes; biopolymers and the derivatives thereof e.g. cellulose, cellulose ethers and esters such as ethylcellulose, nitrocellulose, cellulose acetate and cellulose butyrate, starch, chitin, chitosan, gelatin, zein; natural resins; synthetic resins such as alkyd resins, acrylic resins, phenolic resins, epoxide resins, aminoformaldehyde resins such as urea/formaldehyde resins and melamine/formaldehyde resin; vulcanized rubber; casein; silicone and silicone resins; rubber, chlorinated rubber; and also polymers which are used, for example, as binders in paint systems, such as novolaks which are derived from $C_1$–$C_6$-aldehydes such as formaldehyde and acetaldehyde and a binuclear or mononuclear, preferably mononuclear, phenol which, if desired, is substituted by one or two $C_1$–$C_9$alkyl groups, one or two halogen atoms or one phenyl ring, such as o-, m- or p-cresol, xylene, p-tert.-butylphenol, o-, m- or p-nonylphenol, p-chlorophenol or p-phenylphenol, or a compound having more than one phenolic group such as resorcinol, bis(4-hydroxyphenyl)methane or 2,2-bis(4-hydroxyphenyl)propane; as well as suitable mixtures of said materials.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic materials may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the inventive fluorescent DPPs I or III are used for the mass coloration of polyvinyl chloride, polyamides and, especially, polyolefins such as polyethylene and polypropylene as well as for the preparation of paint systems, including powder coatings, inks, printing inks, color filters and coating colors.

Illustrative examples of preferred binders for paint systems are alkyd/melamine resin paints, acryl/melamine resin paints, cellulose acetate/cellulose butyrate paints and two-pack system lacquers based on acrylic resins which are crosslinkable with polyisocyanate.

According to observations made to date, the inventive fluorescent DPPs I or III can be added in any desired amount to the material to be colored, depending on the end use requirements. In the case of high molecular weight organic materials, for example, the fluorescent DPPs I or III prepared according to this invention can be used in an amount in the range from 0.01 to 40, preferably from 0.01 to 5% by weight, based on the total weight of the colored high molecular weight organic material.

Hence, another embodiment of the present invention relates to a composition comprising
(a) 0.01 to 50, preferably 0.01 to 5, particularly preferred 0.01 to 2% by weight, based on the total weight of the colored high molecular organic material, of a fluorescent DPP I or III according to the present invention, and
(b) 99.99 to 50, preferably 99.99 to 95, particularly preferred 99.99 to 98% by weight, based on the total weight of the colored high molecular organic material, of a high molecular organic material, and
(c) if desired, customary additives such as rheology improvers, dispersants, fillers, paint auxiliaries, siccatives, plasticizers, UV-stabilizers, and/or additional pigments or corresponding precursors in effective amounts, such as e.g. from 0 to 50% by weight, based on the total Weight of (a) and (b).

To produce non-brittle mouldings or to diminish their brittleness, so-called plasticizers can be added to the high molecular weight organic materials prior to moulding. Plasticizers may be, for example, esters of phosphoric acid, phthalic acid and sebacic acid. Said plasticizers may be added before, during or after pigmenting the high molecular weight organic materials with the inventive fluorescent DPPs I or III.

To obtain different shades, the inventive fluorescent DPPs I or III may advantageously be used in admixture with fillers, transparent and opaque white, colored and/or black pigments as well as customary luster pigments in the desired amount.

For the preparation of paints systems, coating materials, color filters, inks and printing inks, the corresponding high molecular weight organic materials, such as binders, synthetic resin dispersions etc. and the inventive fluorescent DPPs I or III are usually dispersed or dissolved together, if desired together with customary additives such as dispersants, fillers, paint auxiliaries, siccatives, plasticizers and/or additional pigments or pigment precursors, in a common solvent or mixture of solvents. This can be achieved by dispersing or dissolving the individual components by themselves, or also several components together, and only then bringing all components together, or by adding everything together at once.

Hence, a further embodiment of the present invention relates to a method of using the inventive fluorescent DPPs I or III for the preparation of dispersions and the corresponding dispersions, and paint systems, coating materials, color filters, inks and printing inks comprising the inventive fluorescent DPPs I or III.

A particularly preferred embodiment relates to the use of the inventive DPPs I or III for the preparation of fluorescent tracers for e.g. leak detection of fluids such as lubricants, cooling systems etc., as well as to fluorescent tracers or lubricants comprising the inventive DPPs I or III. Usually, such lubricant compositions, e.g. for a refrigerant, comprise an oil selected from the group consisting of naphthalenic oils, paraffinic oils, alkylated benzene oils, polyalkyl silicate oils, polyglycols, esters, polyether polyols, polyvinyl ethers, polycarbonates, fluorinated silicones, perfluoroethers, aromatic compounds with fluoroalkyloxy or fluoroalkylthio substituents. The amount of the inventive DPP I or III in the lubricant is chosen generally in an amount of from 100 to 1000 ppm. If the inventive compound I is water-soluble, it could be used as tracer in water as well.

A particular embodiment of this invention concerns ink jet inks comprising the inventive fluorescent compositions The desired ink may contain up to 30% by weight of the fluorescent composition, but will generally be in the range of 0.1 to 10, preferably from 0.1 to 8% by weight of the total ink composition for most thermal ink jet printing applications.

Further, the inks usually contain polymeric dispersants such as random, block, branched or graft polymers or copolymers. Most preferred are polymeric dispersants made by the group transfer polymerization process, because in general these are free from higher molecular weight species that tend to plug pen nozzles.

In AB or BAB block copolymers, the A segment usually is a hydrophobic homopolymer or copolymer which serves to link with the inventive fluorescent composition and the B block generally is a hydrophilic homopolymer or copolymer, or salts thereof and serves to disperse the pigment in the preferably chosen aqueous medium. Such polymeric dispersants and the synthesis thereof are known from e.g. U.S. Pat. No. 5,085,698.

ABC triblocks are also useful as dispersants. In the ABC triblock, the A block usually is a polymer compatible with water, the B block is a polymer capable of binding to the fluorescent composition and the C block is compatible with the organic solvent. Preferably the A and C blocks are end blocks. ABC triblocks and their synthesis are disclosed e.g. in EP-A 556,649. Suitable graft polymers are disclosed in U.S. Pat. No. 5,231,131.

Representative compounds useful for this purpose include e.g. polymers of polyvinyl alcohol, cellulosics and ethylene oxide modified polymers, and dispersant compounds containing ionisable groups such as acrylic acid, maleic acid or sulfonic acid.

The polymeric dispersant is generally present in an amount in the range of from 0.1 to 30, preferably from 0.1 to 8% by weight of the total ink composition.

In addition to, or in place of the preferred polymeric dispersants, surfactants may be used as dispersants. These may be anionic, nonionic, or amphoteric surfactants. A detailed list of non-polymeric as well as some polymeric dispersants is disclosed in the section on dispersants of Manufacturing Confection Publishing Co., (1990) p. 110–129, McCutcheon's Functional Materials, North America Edition.

Usually the ink contains an aqueous medium such as water or a mixture of water and at least one water-soluble organic solvent. Water-soluble organic solvents are well known, representative examples of which are disclosed in e.g. U.S. Pat. No. 5,085,698. Selection of a suitable mixture of water and water-soluble organic solvent depends on usually requirements of the specific application such as desired surface tension and viscosity, drying time of the ink, and the media substrate onto which the ink will be printed.

Particularly preferred is a mixture of a water-soluble solvent having at least two hydroxyl groups, e.g. diethylene glycol, and water, especially deionized water.

In the event that a mixture of water and a water-soluble organic solvent is used as aqueous medium, water usually would comprise from 30 to 95, preferably 60 to 95% by weight, based on the total weight of the aqueous medium.

The amount of aqueous medium generally is in the range of from 70 to 99.8, preferably from 84 to 99.8%, based on the total weight of the ink.

The ink may contain other ingredients well known to those skilled in the art such as surfactants to alter surface tension as well as to maximize penetration. However, because surfactants may destabilize dispersions, care should be taken to insure compatibility of the surfactant with the other ink components. In general, in aqueous inks, the surfactants may be present in amounts ranging from 0.01 to 5, preferably from 0.2 to 3% by weight, based on the total weight of the ink.

Biocides may be used in the ink compositions to inhibit growth of microorganisms. Sequestering agents such as EDTA may also be included to eliminate deleterious effects of heavy metal impurities. Other known additives, such as viscosity modifiers may also be added.

A further embodiment concerns the use of the inventive fluorescent compounds I in phase change ink jet inks. The preparation of such inks is well known in the art, e.g. described in detail in EP-A 816, 410.

For the pigmentation of high molecular weight organic material, the inventive DPPs I or III, optionally in the form of masterbatches, usually are mixed with the high molecular weight organic materials using roll mills, mixing apparatus or grinding apparatus. Generally, the pigmented material is subsequently brought into the desired final form by conventional processes, such as calandering, compression molding, extrusion, spreading, casting or injection molding. In order to prepare non-rigid moldings or to reduce their brittleness it is often desired to incorporate so-called plasticizers into the high molecular weight organic materials prior to forming. Examples of compounds which can be used as such plasticizers are esters of phosphoric acid, phthalic acid or sebacic acid. The plasticizers can be added before or after the incorporation of the inventive DPPs I or III into the polymers. It is also possible, in order to achieve different hues, to add fillers or other coloring constituents such as white, color or black pigments in desired amounts to the high molecular weight organic materials in addition to the inventive DPPs I or III.

For pigmenting lacquers, coating materials and printing inks the high molecular weight organic materials and the inventive DPPs I or III, alone or together with additives, such as fillers, other pigments, siccatives or plasticizers, are generally dissolved or dispersed in a common organic solvent or solvent mixture. In this case it is possible to adopt a procedure whereby the individual components are dispersed or dissolved individually or else two or more are dispersed or dissolved together and only then are all of the components combined.

The present invention additionally relates to inks comprising a coloristically effective amount of the pigment dispersion of the inventive DPPs I or III.

Processes for producing inks especially for ink jet printing are generally known and are described for example in U.S. Pat. No. 5,106,412.

The inks can be prepared, for example, by mixing the pigment dispersions comprising the inventive DPPs I or III with polymeric dispersants.

The mixing of the pigment dispersions with the polymeric dispersant takes place preferably in accordance with generally known methods of mixing, such as stirring or mechanical mixing; it is preferably advisable to use intensive mechanical mixers such as the so-called ULTRATURAX® stirrer from Kunkel & Jahn, Staufen (Germany).

When mixing a DPP I or III with polymeric dispersants it is preferred to use a water-dilutable organic solvent.

The weight ratio of the pigment dispersion to the ink in general is chosen in the range of from 0.001 to 75% by weight, preferably from 0.01 to 50% by weight, based on the overall weight of the ink.

Examples of suitable polymeric dispersants are carboxyl-containing polyacrylic resins such as polymeric methacrylic or crotonic acids especially those obtained by addition polymerization of acrylic acid or acrylic acid and other acrylic monomers such as acrylates.

Depending on the field of use or when using DPP I or III, it is also possible, if desired, to admix a small proportion of a water-miscible organic solvent in from 0.01 to 30% by weight, based on the overall weight of the ink, and/or to admix water and/or bases so as to give a pH in the range from 7 to 11. It may likewise be advantageous to add preservatives, antifoams, surfactants, light stabilizers and pH regulators, for example, to the ink of the invention, depending on the field of use.

Examples of suitable pH regulators are inorganic salts such as lithium hydroxide or lithium carbonate, quaternary ammonium hydroxide or ammonium carbonate. Examples of preservatives and antifoams are, for example, sodium dehydroacetate, 2,2-dimethyl-6-acetoxydioxane or ammonium thioglycolate. It is also possible to employ known agents which regulate the viscosity or the surface tension and are described in e.g. U.S. Pat. No. 5,085,698.

Examples of water-miscible organic solvents are aliphatic $C_1$–$C_4$ alcohols, such as methanol, ethanol, n-propanol, isopropanol, n-butanol, tert.-butanol, ketones such as acetone methyl ethyl ketone, methyl isobutyl ketone or diacetone alcohol, and also polyols, Cellosolves® and carbitols, such as ethylene glycol, diethylene glycol, triethylene glycol, glycerol, propylene gylcol, ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, and also N-methyl-2-pyrrolidone, 2-pyrrolidone, N,N'-dimethylformamide or N,N'-dimethylacetamide.

If desired, the ink prepared as described above can be worked up further. The working up of the ink can be carried out by the customary methods for working up dispersions, by separation techniques, such as sieving or centrifuging the coarse particles from the resulting dispersion. It has been found advantageous, too, to carry out centrifuging in two stages of different intensity, e.g. centrifuging in a first step for from ten minutes to one hour at from 2000 to 4000 rpm and then, in a second step, for from 10 minutes to one hour at from 6000 to 10000 rpm.

Following centrifuging or sieving, the dispersion usually can be used directly as an ink for ink jet printing, for example.

The present invention additionally relates to a process for producing color filters comprising a transparent substrate and applied thereon a red, blue and green layer in any desired sequence, by using a red compound I and known blue and green compounds. The different colored layers preferably exhibit patterns such that over at least 5% of their respective surface they do not overlap and with very particular preference do not overlap at all.

The preparation and use of color filters or color-pigmented high molecular weight organic materials are well-known in the art and described e.g. in Displays 14/2, 1151 (1993), EP-A 784085, or GB-A 2,310,072.

The color filters can be coated for example using inks, especially printing inks, which can comprise pigment dispersions comprising the inventive DPPs I or III or can be prepared for example by mixing a pigment dispersion comprising a DPP I or III with chemically, thermally or photolytically structurable high molecular weight organic material (so-called resist). The subsequent preparation can be carried out, for example, in analogy to EP-A 654 711 by application to a substrate, such as a LCD, subsequent photostructuring and development.

Particular preference for the production of color filters is given to pigment dispersions comprising a DPP I or III which possess non-aqueous solvents or dispersion media for polymers.

The present invention relates, moreover, to toners comprising a pigment dispersion containing a DPP I or III or a high molecular weight organic material pigmented with a DPP I or III in a coloristically effective amount.

In a particular embodiment of the process of the invention, toners, coating materials, inks or colored plastics are prepared by processing masterbatches of toners, coating materials, inks or colored plastics in roll mills, mixing apparatus or grinding apparatus.

The present invention additionally relates to colorants, colored plastics, polymeric ink particles, or non-impact-printing material comprising an inventive DPP I or III pigment, preferably in the form of a dispersion, or a high molecular weight organic material pigmented with a DPP I or III in a coloristically effective amount.

A coloristically effective amount of the pigment dispersion according to this invention comprising an inventive DPP I or III denotes in general from 0.0001 to 99.99% by weight, preferably from 0.001 to 50% by weight and, with particular preference, from 0.01 to 50% by weight, based on the overall weight of the material pigmented therewith.

Further, the inventive compounds I can be used for textile application and for the dying of paper.

Another preferred embodiment concerns to the use of the inventive compounds for color changing media. There are three major techniques in order to realize full-color organic electroluminescent devices:
(i) to use the three primary colors blue, red and green by electroluminescence,
(ii) to convert electroluminescent blue to photoluminescent green and red via color changing media which absorb the above electroluminescent blue and fluoresce in green and red,
(iii) to convert white electroluminescent emission to blue, green and red via classical color filters.

The inventive compounds are useful for EL materials for the above category (i). In addition, the inventive compounds are also useful for the above technique (ii). This is because the invented compounds can exhibit strong photoluminescence as well as electroluminescence.

Technique (ii) is known for example from U.S. Pat. No. 5,126,214 in which a method is described wherein EL blue with a maximum wavelength of ca. 480 nm to green, yellowish green, orange and red using coumarin, 4-(dicyanomethylene)-2-methyl-6-(p-dimethylaminostyryl)-4H-pyran, pyridine, rhodamine 6G, phenoxazone and other dyes.

In contrast to known red fluorescent dyes (thioindigos) the inventive DPPs I or III can be applied to color polyamides, because they do not decompose during the incorporation into the polyamides. Further, they exhibit an exceptionally good lightfastness, a superior heat stability, especially in plastics.

EXAMPLES

The solid state absorbance spectra are measured on a Perkin-Elmer Lambda 9 UV/VIS-spectrometer and the solid state fluorescence spectra on a Perkin-Elmer MPF 66 with a 5 cm Ulbricht-sphere. The measurements are carried out with flexible PVC containing 0.02% by weight of the inventive compounds.

Example 1

Sodium hydride (60% dispersion in mineral oil, 47 g, 1.175 mol) is added portionwise over a 30-minutes period without external cooling and under nitrogen to a slurry of 1,4-diketo-3,6-bis-(4'-t-butylphenyl)pyrrolo[3,4-c]pyrrole (140 g, 0.33 mol) in 1-methyl-2-pyrrolidone (2 liters). After two hours the reaction mixture is cooled in an ice-water bath for 30 minutes, then benzyl bromide (216 g, 1.263 mol) is added dropwise (over 30 minutes). The reaction mixture is then slowly warmed-up to room temperature (by keeping the reaction flask in the cooling bath and allowing the ice in the bath to melt) and stirred at this temperature for 10 hours. Then acetic acid (50 ml), water (50 ml) and acetone (1.5 liters) are successively added. After stirring for 1 hour, a red solid is filtered off, washed with acetone (500 ml), water (4 liters), ethanol (1 liter), hexane (1 liter) and acetone (500 ml) and then dried under a reduced atmosphere at 50° C. for 24 hours. Yield: 104 g (53%) of bright red solid 1,4-diketo-2,5-dibenzyl-3,6-bis-(4'-butylphenyl)pyrrolo[3,4-c]pyrrole.

Example 2

Example 1 is repeated except that 1,4-diketo-3,6-bis-(4'-chlorophenyl)pyrrolo-[3,4-c]pyrrole is used and then 1,4-diketo-2,5-dibenzyl-3,6-di-(4'-chloro-phenyl)pyrrolo[3,4-c]pyrrole is obtained. Yield: 58%

Example 3

Sodium hydride (60% by weight in mineral oil, 3.84 g, 0.088 mol) is added portionwise to di-(4-chlorophenyl) diselenide (16.76 g, 0.044 mol) in DMF (200 ml) at room temperature under an atmosphere of nitrogen. The reaction mixture is then heated in an oil bath at 70° C. for one hour, then 1,4-diketo-2,5-dibenzyl-3,6-di-(4'-chloro-phenyl)pyrrolo[3,4-c]pyrrole (obtained according to example 2) (21.5 g, 0.040 mol) is added and the reaction mixture is heated to 140° C. for five hours. After cooling to room temperature, water (500 ml) is added and the reaction mixture is heated to 100° C. for 30 min. The obtained solid is filtered off, washed with water, then ethanol, and finally dried under an atmosphere of reduced pressure at a temperature of 500° C. for 24 hours.

Yield: 96% (32.44 g, 0.038 mol) of dark red solid 1,4-diketo-2,5-dibenzyl-3,6-di-(4'-(4"-chlorophenylselenyl) phenyl)pyrrolo[3,4-c]pyrrole with a melting point in the range of from 248 to 250° C.

Example 4

Example 1 is repeated except that n-butyl iodide is used as alkylating agent Yield: 33%.

Example 5

Example 4 is repeated except that 1,4-diketo-3,6-bis-(4'-methylphenyl)pyrrolo-[3,4-c]pyrrole used Yield: 54%.

Example 6

Example 5 is repeated except that 1,4-diketo-3,6-bis-(4'-biphenyl)pyrrolo[3,4-c]pyrrole is used. Yield: 58%.

Example 7

Example 6 is repeated except that 2-naphthylmethyl bromide is used as alkylating agent. Yield: 51%.

Example 8

Example 1 is repeated except that 1,4-diketo-3,6-bis-(4-(4-morpholinyl)phenyl)-pyrrolo[3,4-c]pyrrol (obtained according to example 4 of EP-A 353,184) is used. Yield: 64%.

Example 9

Example 7 is repeated except that 1,4-diketo-3,6-bis-(4-(4-morpholinyl)phenyl)-pyrrolo[3,4-c]pyrrol is used. Yield: 19%.

Example 10

(a) Triphenyl amine (98.32 g, 0.393 mol) is suspended in DMF (280 ml). Phosphorus oxychloride (66.24 g, 0.432 mol) is added dropwise to it over a 30-minutes period without external cooling. After stirring for one more hour, the reaction is heated to 80° C. (bath temperature) for 2½ hours. After cooling to room temperature, the reaction is slowly poured onto ice-cold water (8 liters) with vigorous stirring. After 30 minutes, aqueous sodium hydroxide (5 N, 250 ml) is added to the reaction, and stirring is continued for one hour. The obtained precipitate is filtered off, washed-with water (2 liters), then with methanol (2 litres) and dried to give 4-diphenylaminobenzaldehyde as a beige solid (90.47 g, 0.331 mol, 84%), which is used in the next step without further purification.

(b) 48.7 g of the above obtained 4-diphenylaminobenzaldehyde (0.178 mol) is suspended in formic acid (400 ml). Hydroxylamine sulfate is added (116.08 g, 0.098 mol), followed by sodium formiate (14.15 g, 0.214 mol). The reaction is heated under reflux for 3 hours. Then the solvent is removed under vacuum. The residue is suspended in toluene (800 ml). The residual solid is filtered off and discarded. Solvents are evaporated and the residue is dissolved in a minimum amount of dichloromethane. This solution is filtered through a pad of silica gel, using dichloromethane as solvent. The solvent is then evaporated under vacuum. The thus obtained solid is taken up in toluene (350 ml) and heated to reflux in the presence of charcoal. After filtering hot, the solvent is removed from the filtrate to give 4-diphenylaminobenzonitrile (42.01 g, 0.155 mol, 87%) as a beige solid, which is taken to the next step without further purification.

(c) Sodium pieces (24.5 g, 1.064 mol) are added to tert.-amyl alcohol (400 ml). Then 20 mg of anhydrous $FeCl_3$ are added. The reaction mixture is slowly heated until a gentle reflux is obtained. After two hours, all sodium is reacted. 134.54 g of the above obtained 4-diphenylaminobenzonitrile (0.501 mol) are added in portions over a period of 15 minutes. Then di-tert.-butyl succinate (79.5 g, 0.346 mol) in tert.-amyl alcohol (300 ml) is added over 1.75 hours. After an additional hour of heating to reflux, the reaction mixture is cooled to room temperature and stirred overnight. Then, the reaction mixture is slowly added into a mixture of water (1200 ml) and methanol (600 ml) and stirred for 3 hours. The thus obtained solid is then filtered, washed with first water and then ethanol, and afterwards dried at 50° C. overnight. 70.96 g (0.114 mol, 46%) of 1,4-diketo-3,6-bis-(4-diphenylaminophenyl)-pyrrolo[3,4-c] pyrrole are obtained as a violet powder. $^1$H-NMR (300 MHz, $d^6$-DMSO): 6.91 (d, 4H, J=9 Hz); 7.15–7.22 (m, 12H); 7.38–7.43 (m, 8H); 8.32 (d, 4H, J=9 Hz); 11.02 (broad s, 2H).

(d) Example 1 is repeated except that the above obtained 1,4-diketo-3,6-bis-(4-diphenylaminophenyl)pyrrolo[3,4-c] pyrrol is used. Yield: 56%.

Example 11

1.02 g (2.3 mmol) 1,4-diketo-3,6-bis-(4-biphenyl)-pyrrolo-(3,4-c)-pyrrole is slurred in 15 ml of 1-methyl-2-pyrrolidinone for 2 hours at room temperature. 0.35 g of sodium hydride (60–72% dispersion in mineral oil) is added to the slurry under nitrogen. After stirring for 2 hours, 1.62 g (6.6 mmol) of 2-phenylbenzyl bromide is added to the reaction mixture and then the mixture is stirred additionally for 2 hours. The mixture was poured into 50 ml of water and the red solid is filtered off and purified by column chromatography (silica gel, dichloromethane as eluent). After dried, 0.327 g (18%) of a red solid is obtained.

Example 12

Example 11 is repeated except that 4-tert-butylbenzyl bromide is used as alkylating agent. Red solid (Yield: 63%).

Example 13

2.09 g (4.75 mmol) 1,4-diketo-3,6-bis-(4-biphenyl)-pyrrolo-(3,4-c)-pyrrole are slurred in 30 ml of 1-methyl-2-pyrrrolidinone for 2 hours at room temperature. 1.29 g (11.52 mmol) of potassium tert.-butoxide are added to the slurry under nitrogen. After stirring for 2 hours, 2.05 g (11.1 mmol) of 3-methylbenzyl bromide are added to the reaction mixture and then the mixture is stirred additionally for 2 hours. The mixture is poured into 50 ml of water and the red solid is filtered off and purified by column chromatography (silica gel, dichloromethane as eluent). After drying, 1.89 g (61%) of a red solid are obtained.

Example 14 example 11 is repeated except that 1,4-diketo-3,6-bis-(4-methylphenyl)-pyrrolo-(3,4-c)-pyrrole is used as starting material. Red solid (Yield 18%).

Example 15 example 14 is repeated except that 4-tert-butylbenzyl bromide is used as alkylating agent. Red solid (Yield: 13%).

Example 16

Example 14 is repeated except that 2-methylbenzyl bromide is used as alkylating agent. Red solid (Yield: 27%).

Example 17

Example 14 is repeated except that 3-methylbenzyl bromide is used as alkylating agent. Red solid (Yield: 9.3%).

Example 18

Example 13 is repeated except that 3,5-dimethylbenzyl bromide is used as alkylating agent. Red solid (Yield: 24%).

Example 19

Example 14 is repeated except that 3,5-dimethylbenzyl bromide is used as alkylating agent. Red solid (Yield: 54%).

Example 20

Example 13 is repeated except that 4-methyl benzylbromide is used as alkylating agent. Red solid (Yield: 62%).

Example 21 example 14 is repeated except that 4-methylbenzyl bromide is used as alkylating agent. Red solid (Yield: 57%).

Example 22

24.6 g of potassium tert.-butoxide, 30 g of 2-naphthonitrile and 200 ml of tert.-amyl alcohol are heated up to 100° C. under a nitrogen atmosphere. As soon as the this temperature has been reached, a solution of 23 g of di-n-butyl succinate and 70 ml of tert.-amyl alcohol is added over 1 hour using a dropping funnel. When the addition is completed, the reaction mixture is kept for 16 hours at 100° C., then cooled to 65° C., neutralized with 20 ml of glacial acetic acid and boiled briefly to reflux. The resultant pigment suspension is filtered at room temperature. The filter cake is suspended in 300 ml of methanol and the pigment is isolated again by filtration, then finally washed with methanol and water until washings run colourless, and dried at 100° C. in an atmosphere under reduced pressure affording 26.1 g (69% of theory, based on dibutyl succinate) of pure pigment of 1,4-diketo-3,6-bis-(2-naphthyl)-pyrrolo-(3,4-c)-pyrrole.

And then, Example 18 is repeated except that 1,4-diketo-3,6-bis-(2-naphthyl)-pyrrolo-(3,4-c)-pyrrole is used as starting material. Red solid (Yield: 36%).

Example 23

Example 22 is repeated except that benzyl bromide is used as alkylating agent. Orange solid (Yield: 30%).

Example 24

Example 22 is repeated except that 2-methylbenzyl bromide is used as alkylating agent. Orange solid (Yield: 30%).

Example 25

Example 22 is repeated except that 2-phenylbenzyl bromide is used as alkylating agent. Red solid (Yield: 8%).

Example 26

Example 13 is repeated except that 4-phenylbenzyl bromide is used as alkylating agent. Red solid (Yield: 50%).

Example 27

2.0 g (4.54 mmol) 1,4-diketo-3,6-bis-(4-biphenyl)-pyrrolo-(3,4-c)-pyrrole are slurred in 30 ml of 1-methyl-2-pyrrrolidinone for 2 hours at room temperature. 1.3 g (11.61 mmol) of potassium tert.-butoxide are added to the slurry under nitrogen. After stirring for 2 hours, 2.07 g (11.2 mmol) of 2-methylbenzyl bromide are added to the reaction mixture and then the mixture is stirred additionally for 2 hours. The mixture is poured into 50 ml of water and the red solid is filtered off and purified by column chromatography (silica gel, dichloromethane as eluent). After drying, 0.866 g (29%) of a red solid are obtained.

Example 28

Example 27 is repeated except that 3-phenylbenzyl bromide is used as alkylating agent. Red solid (Yield: 38%).

Example 29

Example 22 is repeated except that 3-methylbenzyl bromide and 1,4-diketo-3,6-bis-(2-naphthyl)-pyrrolo-(3,4-c)-pyrrole are used as alkylating agent and starting material, respectively. Red solid (Yield: 30%).

Example 30

And then, Example 29 is repeated except that 4-methylbnzyl bromide is used as alkylating agent. Red solid (Yield: 36%).

Example 31

Example 29 is repeated except that 4-phenylbenzyl bromide is used as alkylating agent. Orange solid (Yield: 30%).

Example 32

Example 31 is repeated except that 1,4-diketo-3,6-bis-(4-methylphenyl)-pyrrolo-(3,4-c)-pyrrole is used as starting material. Red solid (Yield: 30%).

Example 33

Example 27 is repeated except that 1-bromoethyl benzene is used as alkylating agent. Yellow solid (Yield: 11.4%).

Example 34

Example 33 is repeated except that 1,4-diketo-3,6-bis-(4-methylphenyl)-pyrrolo-(3,4-c)-pyrrole is used as starting material. Yellow solid (Yield: 35%).

Example 35

9.2 g of potassium tert.-butoxide, 15 g of 6-methoxy-2-naphthonitrile and 80 ml of tert.-amyl alcohol are heated up to 100° C. under a nitrogen atmosphere. As soon as the this temperature is reached, a solution of 9.4 g of di-n-butyl succinate and 20 ml of tert.-amyl alcohol is added over 1 hour using a dropping funnel. When the addition is completed, the reaction mixture is kept for 12 hours at 100° C., then cooled to 65° C., neutralized with 20 ml of glacial acetic acid and boiled briefly to reflux. The resultant pigment suspension is filtered at room temperature. The filter cake is suspended in 300 ml of methanol and the pigment is isolated again by filtration, then finally washed with methanol and water until washings run colourless, and dried at 100° C. in an atmosphere under reduced pressure which affords 4.2 g (23% of theory, based on dibutyl succinate) of 1,4-diketo-3,6-bis-(2-(6-methoxynaphthyl))-pyrrolo-(3,4-c)-pyrrole.

Example 29 is repeated except that 1,4-diketo-3,6-bis-(6-methoxy-2-naphthyl)-pyrrolo-(3,4-c)-pyrrole are used as starting material. Yellow solid (Yield: 21%).

Example 36

Example 35 is repeated except that 3,5-dimethylbenzyl bromide is used as alkylating agent. Yellow solid (Yield: 38%).

Example 37

2.2 g (5.0 mmol) 1,4-diketo-3,6-bis-(4-biphenyl)-pyrrolo-(3,4-c)-pyrrole are slurred in 20 ml of 1-methyl-2-pyrrrolidinone for 2 hours at room temperature. 1.4 g (13.0 mmol) of potassium t-butoxide are added to the slurry under nitrogen. After stirring for 2 hours, 2.78 g (12 mmol) of (2-iodoethyl) benzene are added to the reaction mixture. The mixture is heated up to 80° C. and stirred additionally for 3 hours. After cooling to room temperature, the mixture is poured into 50 ml of water and a red solid is filtered off and purified by column chromatography (silica gel, dichloromethane as eluent). After drying, 0.16 g (5%) of a red solid are obtained.

Example 38

Example 37 is repeated except that 1,4-diketo-3,6-bis-(2-naphthyl)-pyrrolo-(3,4-c)-pyrrole is used as starting material (Yield: 29%).

Example 39

Example 32 is repeated except that 3-methoxylbenzyl bromide is used as alkylating agent. Yellow solid (Yield: 38%).

Example 40

Example 27 is repeated except that 3-methoxylbenzyl bromide is used as alkylating agent. Yellow solid (Yield: 49%).

Example 41

Example 32 is repeated except that 3-phenylbenzyl bromide is used as alkylating agent. Yellow solid (Yield: 33%).

Example 42

Example 29 is repeated except that 3-phenylbenzyl bromide is used as alkylating agent. Orange solid (Yield: 35%).

Example 43

Example 27 is repeated except that 3-chlorobenzyl bromide is used as alkylating agent. Yellow solid (Yield: 52%).

Example 44

Example 27 is repeated except that 3,4-dichlorobenzyl bromide is used as alkylating agent. Yellow solid (Yield: 36%).

Example 45

Example 29 is repeated except that 3-methoxybenzyl bromide is used as alkylating agent. Orange solid (Yield: 30%).

Example 46

50.4 g (0.45 mol) of potassium tert.-butoxide, 50 g of 3-tolunitrile and 300 ml of tert.-amyl alcohol are heated up to 100° C. under a nitrogen atmosphere. As soon as the this temperature is reached, a solution of 50.6 g (0.22 mol) of di-n-butyl succinate and 50 ml of tert.-amyl alcohol are added over 1 hour using a dropping funnel. When the addition is completed, the reaction mixture is kept for 19 hours at 100° C., then cooled to 65° C., neutralized with 40 ml of glacial acetic acid and boiled briefly to reflux. The resultant pigment suspension is filtered at room temperature. The filter cake is suspended in 300 ml of methanol and the pigment is isolated again by filtration, then finally washed with methanol and water until washings run colourless, and dried at 100° C. in an atmosphere under reduced pressure which affords 28.8 g (42% of theory, based on dibutyl succinate) of 1,4-diketo-3,6-bis-(3-methylphenyl)-pyrrolo-(3,4-c)-pyrrole.

Example 29 is repeated except that 1,4-diketo-3,6-bis-(3-methylphenyl)-pyrrolo-(3,4-c)-pyrrole is used as starting material. Yellow solid (Yield: 34%).

Example 47

Example 46 is repeated except that 3,5-dimethylbenzyl bromide is used as alkylating agent. Yellow solid (Yield: 42%).

Example 48

53 g (0.47 mol) of potassium tert.-butoxide, 50 g (0.38 mol) of 3-methoxybenzonitrile and 250 ml of tert.-amyl alcohol are heated up to 100° C. under a nitrogen atmosphere. As soon as the this temperature has been reached, a solution of 50.6 g (0.22 mol) of di-n-butyl succinate and 50 ml of tert.-amyl alcohol is added over 1 hour using a dropping funnel. When the addition is completed, the reaction mixture is kept for 20 hours at 100° C., then cooled to 65° C., neutralized with 35 ml of glacial acetic acid and boiled briefly to reflux. The resultant pigment suspension is filtered at room temperature. The filter cake is suspended in 500 ml of water and the pigment is isolated again by filtration, then finally washed with methanol and water until washings run colourless, and dried at 100° C. in an atmosphere under reduced pressure which affords 42.3 g (65% of theory, based on dibutyl succinate) of 1,4-diketo-3,6-bis-(3-methoxylphenyl)-pyrrolo-(3,4-c)-pyrrole.

Example 29 is repeated except that 1,4-diketo-3,6-bis-(3-methoxylphenyl)-pyrrolo-(3,4-c)-pyrrole is used as starting material. Yellow solid (Yield: 45%).

Example 49

Example 48 is repeated except that 3,5-dimethylbenzyl bromide is used as alkylating agent. Yellow solid (Yield: 38%).

Example 50

Example 32 is repeated except that 3,5-di-tert-butylbenzyl bromide is used as alkylating agent. Yellow solid (Yield: 27%).

Example 51

2.2 g (5.0 mmol) 1,4-diketo-3,6-bis-(4-biphenyl)-pyrrolo-(3,4-c)-pyrrole are slurred in 20 ml of 1-methyl-2-pyrrroli-dinone for 2 hours at room temperature. 1.46 g (13.0 mmol) of potassium tert.-butoxide are added to the slurry under nitrogen. After stirring for 2 hours, 2.53 g (13 mmol) of neopentyl iodide is added to the reaction mixture. The mixture is heated up to 120° C. and stirred additionally for 12 hours. After cooling to room temperature, the mixture is poured into 50 ml of water and a red solid is filtered off and purified by column chromatography (silica gel, dichloromethane as eluent). After drying, 0.13 g (4%) of an orange solid are obtained.

Example 52

1.87 g (5.0 mmol) 1,4-diketo-3,6-bis-(4-dimethylaminophenyl)-pyrrolo-(3,4-c)-pyrrole are slurred in 60 ml of 1-methyl-2-pyrrrolidinone for 2 hours at room temperature. 1.68 g (15.0 mmol) of potassium tert.-butoxide are added to the slurry under nitrogen. After stirring for 2 hours, 2.78 g (15 mmol) of 1-bromoethyl benzene are added to the reaction mixture. The mixture is then heated up to 80° C. and stirred additionally for 2 hours. After cooling to room temperature, the mixture is poured into 50 ml of water and a red solid is filtered off and purified by column chromatography (silica gel, dichloromethane as eluent). After drying, 0.2 g (10%) of a red solid are obtained.

Example 53

Example 52 is repeated except that 3,5-di-t-butylbenzyl bromide as alkylating agent. Red solid (Yield: 33%).

Example 54

Example 52 is repeated except that 3-bromolbenzyl bromide as alkylating agent. Red solid (Yield: 23%).

Example 55

Example 53 is repeated except that 1,4-diketo-3,6-bis-(6-methoxy-2-naphthyl)-pyrrolo-(3,4-c)-pyrrole is used as starting material. Red solid (Yield: 21%).

Example 56

Example 53 is repeated except that 1,4-diketo-3,6-bis-(4-chlorophenyl)-pyrrolo-(3,4-c)-pyrrole as starting material. Yellow solid (Yield: 25%).

Example 57

Example 53 is repeated except that 1,4-diketo-3,6-bis-(2-naphthyl)-pyrrolo-(3,4-c)-pyrrole as starting material. Red solid (Yield: 23%).

Example 58

Example 53 is repeated except that 1,4-diketo-3,6-bis-(4-biphenyl)-pyrrolo-(3,4-c)-pyrrole and 1-bromo-n-propyl benzene as starting material and alkylating agent, respectively. Red solid (Yield: 5%).

Example 59

6.7 g (60 mmol) of potassium tert.-butoxide, 10.7 g (52 mmol) of 4-cyano-trans-stilbene and 100 ml of tert.-amyl alcohol are heated up to 100° C. under a nitrogen atmosphere. As soon as the temperature is reached, a solution of 5.98 g (26 mmol) of di-n-butyl succinate and 50 ml of tert.-amyl alcohol is added over 1 hour using a dropping funnel. When the addition is completed, the reaction mixture is kept for 16 hours at 100° C., then cooled down to 65° C., neutralized with 20 ml of glacial acetic acid and boiled briefly to reflux temperature. The resultant pigment suspension is filtered at room temperature. The filter cake is suspended in 100 ml of methanol and the pigment is isolated by filtration, then finally washed with methanol and water until washings run colourless, and dried at 100° C. in an atmosphere under reduced pressure which affords 2.5 g (20% of theory, based on dibutyl succinate) of pure pigment of 1,4-diketo-3,6-bis-(4-trans-stilbene)-pyrrolo-(3,4-c)-pyrrole.

Example 53 is repeated except that and 1,4-diketo-3,6-bis-(4-trans-stilbene)-pyrrolo-(3,4-c)-pyrrole is used as starting material. Red solid (Yield: 20%).

Example 60

Example 59 is repeated except that 3,5-dimethylbenzyl bromide as alkylating agent. Red solid (Yield: 33%).

Example 61

Sodium hydride (60% dispersion in mineral oil, 47 g, 1.175 mol) is added portionwise over a 30-minutes period without external cooling and under nitrogen to a slurry of 1,4-diketo-3,6-bis-(4'-biphenyl)pyrrolo[3,4-c]pyrrole (140 g, 0.318 mol, obtained according to example 19 of U.S. Pat. No. 4,579,949) in 1-methyl-2-pyrrolidone (2 liters). After two hours the reaction mixture is cooled in an ice-water bath for 30 minutes, then benzyl bromide (216 g, 1.263 mol) is added dropwise (over 30 minutes). The reaction mixture is then slowly warmed-up to room temperature (by keeping the reaction flask in the cooling bath and allowing the ice in the bath to melt) and stirred at this temperature for 60 hours. Then acetic acid (50 ml), water (50 ml) and acetone (1.5 liters) are successively added. After stirring for one hour, a red solid is filtered off, washed with acetone (500 ml), water (4 liters), ethanol (1 liter), hexane (1 liter) and acetone (500 ml) and then dried under an atmosphere of reduced pressure at 50° C. for 24 hours. Yield: 129.50 g (66%) of bright red solid 1,4-diketo-2,5-dibenzyl-3,6-bis-(4'-biphenyl)pyrrolo[3,4-c]pyrrole.

Elemental analysis: C: 83.05% (calc. 85.14%), H: 5.36% (calc. 5.20%), N: 4.15% (calc. 4.51%), max. absorbance (solid state): 557 nm; max. fluorescence (solid state): 557 nm; absorption (max) in toluene (aerated): 492 nm; fluorescence (max) in toluene (aerated): 557 nm; molar absorption coefficient (in toluene): 27579; quantum yield (in toluene): 0.50.

Example 62

Example 61 is repeated except that of 1,4-diketo-3,6-bis-(4-methylphenyl)pyrrolo[3,4-c]pyrrole as starting material. Red solid (Yield: 42%).

Example 63

Example 53 is repeated except that 1,4-diketo-3,6-bis-(4-cis-stilbene)-pyrrolo-(3,4-c)pyrrole is used as starting material. Red solid (Yield: 36%).

Example 64

Example 36 is repeated except that 3-phenylbenzyl bromide as alkylating agent. Red solid (Yield: 25%).

Example 65

Example 46 is repeated except that 1-phenylethyl bromide as alkylating agent. Red solid (Yield: 11%).

Example 66

Example 61 is repeated except that 3,5-di-t-butylbenzyl bromide as alkylating agent. Red solid (Yield: 11%).

Example 67

Example 48 is repeated except that 3,5-di-t-butylbenzyl bromide as alkylating agent. Red solid (Yield: 42%).

Example 68

To the below mentioned engineering plastics (each 400 g) in chip form the inventive compounds (each 0.12 g) are added in a paint shaker and shaken there for 90 seconds. Thereafter, the thus obtained chips comprising the adhered inventive compounds are molded at the temperatures specified in Table 1 below using a BA400 Battenfeld injection molder.

TABLE 1

| | Temperature settings (° C.) | | |
|---|---|---|---|
| Engineering plastic | Nozzle | Middle | Rear |
| HIPS | 232 (450° F.) | 232 (450° F.) | 232 (450° F.) |
| ABS | 232 (450° F.) | 232 (450° F.) | 232 (450° F.) |
| Nylon 6, 12 | 271 (520° F.) | 260 (500° F.) | 254 (490° F.) |
| PMMA | 226 (440° F.) | 226 (440° F.) | 226 (440° F.) |

HIPS: high impact polystyrene (825P1 from Fina Oil and Chemical; melt flow (g/10 min): 8 (reference ASTM TEST 200/5.0 D-1238))

ABS: acrylic-butadiene-styrene copolymer (Natural ABS 3501-002 from Diamond Polymer; melt flow (g/10 min): 7.5 (reference ASTM Method D-1238))

Nylon 6,12: polyamide (ZYTEL®158L from DuPont Engineering Polymers; inherent viscosity: 1.15))

PMMA: polymethylmethacrylate (PLEXIGLASO®V825 from Atohaas; melt flow (g/10 min): 3.7 (reference ASTM Method D-1238))

Five chips (from the same series) obtained from the injection molder are collected after the color is distributed homogeneously.

The color chips are then mounted, with the thickest part of the chip exposed (0.31 cm (0.122 inches)), in a CI35A Atlas Xenon Weather-O-Meter. The parameters of the weather-o-meter are listed in Table 2.

The color chips are then exposed to the weather-o-meter for 100, 250, 500, 750, and 1000 hours. The color chips are rated after each fading interval is reached. The lightfastness is subjectively evaluated using a gray scale rating of 1–5. A rating of 5 indicates no fade or color difference. In cases where the color chip appears to darken a rating of d for darkening is applied to the gray scale rating. In cases where the color chip loses most of its color a rating of f for fading is applied to the gray scale rating.

TABLE 2

Parameters for the fading test
Automatic voltage 0.35 W/m² at 340 nm

| | Light Cycle Settings Temperature [° C.] |
|---|---|
| Black Panel[1] | 63 |
| Wet Bulb Depression[2] | 10 |
| Conditioning Water[3] | 30 | automatic voltage: controls irradiance level (similar to the average irradiance found on a clear summer day in southern Florida)
[1] temperature is measured by a sensor attached to the specimen holder; provides a temperature reading resulting from the chamber air and any heating due to xenon light
[2] difference between air temperature (measured by the so-called dry bulb sensor) and wet bulb temperature (measured by wet bulb sensor, whereby the wet bulb is covered by a moistened wick; due to the cooling effect of evaporation, the wet bulb reading is usually lower than the dry bulb reading (except at 100% relative humidity).

Results

TABLE 3

Nylon evaluation

| used DPP of | Lightfastness evaluation using the gray scale | | | | |
|---|---|---|---|---|---|
| example no. | 100 h | 250 h | 500 h | 700 h | 1000 h |
| 5 | 4/5 | 4/5d | 3/4d | 3/4d | 3/4d |
| 7 | 4/5 | 4/5d | 4f | 3/4f | 2/3f |
| 4 | 4/5 | 4d | 3/4d | 3/4d | 3/4d |

(gray scale assesses color differences after exposure to light, from 1 to 5, wherein 5 means no change in color)

By comparison, the commercial thioindigo Vat Red 41 (Hostasol®Red 5B from Clariant) decomposed in nylon, i.e. no color is found in the produced nylon chips.

TABLE 4

PMMA evaluation

| Used DPP of example no. | Lightfastness evaluation using the gray scale | | | | |
|---|---|---|---|---|---|
| | 100 h | 250 h | 500 h | 700 h | 1000 h |
| 4 | 5 | 5 | 4/5 | 4/5 | 4/5 |
| 5 | 5 | 5 | 4/5 | 4/5 | 4/5 |
| 7 | 5 | 5 | 4/5 | 4/5 | 4/5 |
| 11 | 5 | 4/5 | 4/5 | 4/5 | 4/5 |
| 13b | 5 | 4/5 | 4/5 | 4/5 | 4/5 |
| 15 | 5 | 4d | 4 | 3 | 3f |
| Vat Red 41 | 3f | 2f | 1f at 322 h | | |

TABLE 5

ABS evaluation

| Used DPP of example no. | Lightfastness evaluation using the gray scale | | | | |
|---|---|---|---|---|---|
| | 100 h | 250 h | 500 h | 700 h | 1000 h |
| 4 | 4/5 | 4/5 | 4/5d | 4d | 4d |
| 5 | 4 | 4 | 4d | 4d | 4d |
| 7 | 4 | 4d | 4d | 4d | 4d |
| 11 | 4/5 | 4/5 | 4/5d | 4/5d | 4d |
| 13b | 4/5 | 4/5 | 4/5d | 4/5d | 4d |
| 15 | 4/5 | 3/4d | 3/4d | 3d | 3d |
| Vat Red 41 | 3 | 2 | 1f at 322 h | | |

TABLE 6

HIPS evaluation

| used DPP of example no. | Lightfastness evaluation using the gray scale | | | | |
|---|---|---|---|---|---|
| | 100 h | 250 h | 500 h | 700 h | 1000 h |
| 4 | 4/5 | 4 | 4 | 4d | 3d |
| 5 | 4 | 4 | 3/4 | 3d | 2/3d |
| 7 | 4 | 4 | 3/4 | 3d | 2/3d |
| 10d | 4/5 | 4 | 4d | 3d | 3d |
| 11 | 4/5 | 4/5 | 4 | 4 | 3/4d |
| 13b | 4/5 | 4/5 | 4/5d | 4d | 3/4d |
| 15 | 4/5 | 3/4d | 3/4d | 3d | 3d |
| Vat Red 41 | 3 | 2/3 | 1f | | |

Example 69

On an ITO glass substrate (from Geomatech Co. Ltd., ITO film thickness 200 nm, sheet resistance 10 Ω/cm$^2$), the TPD compound of the following formula

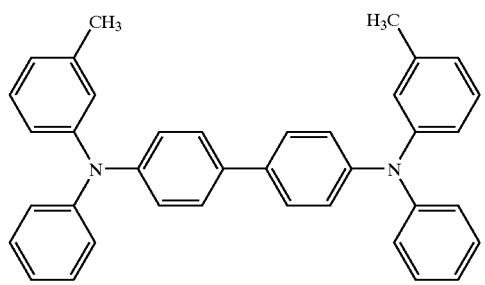

is deposited as a hole transporting substance by vacuum evaporation under a reduced pressure of 6.665×10$^{-4}$ Pa (5.0×10$^{-6}$ Torr) and at a depositing rate of 0.05 nm/sec to a membrane thickness of 50 nm to form a hole transporting layer. Then, on the hole transporting layer thus prepared, the compound of Example 1 is deposited as a light-emitting material under a depositing condition of 6.665×10$^{-4}$ Pa (5.0×10$^{-6}$Torr) and 0.05 nm/sec to a membrane thickness of 50 nm to form a light-emitting layer. Then, on the light-emitting layer, firstly lithium is co-deposited with the above compound at a rate of 0.015 nm/sec to form a 1 nm-thick layer and subsequently aluminum as cathode are deposited on it to a film thickness of 200 nm. By using the ITO side as the anode and the aluminum side as the cathode, a bias of 20 V is applied to the above element. A luminescence showing a luminance of 1410 cd/m$^2$ with the EL emission peak wavelength at 560 nm is confirmed as the average value of the five elements. For evaluation of luminance and emission spectrum, the Luminometer BM-8 manufactured by TOPCON Co, Ltd. and the Multichannel Photodetector IMUC-7000 manufactured by Otsuka Electronics are used, respectively.

Example 70–101

Example 69 is repeated replacing the light-emitting material with the compounds indicated in Table 7 below, summarizing the EL performances also (the results of Example 69 is included also in the table).

TABLE 7

| Example | Light-emitting Material (Example) | EL Emission-Peak Wavelength (nm) | EL Intensity (cd/m$^2$) |
|---|---|---|---|
| 69 | 1 | 560 | 1410 |
| 70 | 2 | 580 | 408 |
| 71 | 5 | 573 | 662 |
| 72 | 7 | 580 | 157 |
| 73 | 11 | 581 | 596 |
| 74 | 12 | 578 | 1184 |
| 75 | 13 | 581 | 4680 |
| 76 | 14 | 576 | 3030 |
| 77 | 15 | 570 | 1932 |
| 78 | 16 | 574 | 2310 |
| 79 | 17 | 569 | 2990 |
| 80 | 18 | 578 | 2670 |
| 81 | 19 | 566 | 5260 |
| 82 | 20 | 581 | 1563 |
| 83 | 21 | 568 | 4110 |
| 84 | 22 | 579 | 1303 |
| 85 | 23 | 579 | 3970 |
| 86 | 24 | 585 | 3340 |
| 87 | 25 | 584 | 430 |
| 88 | 26 | 581 | 398 |
| 89 | 29 | 578 | 2810 |
| 90 | 30 | 577 | 1473 |
| 91 | 31 | 579, 619 | 27 |
| 92 | 33 | 568 | 202 |
| 93 | 34 | 534 | 2600 |
| 94 | 35 | 585 | 1842 |
| 95 | 37 | 581 | 2220 |
| 96 | 39 | 552 | 1648 |
| 97 | 40 | 576 | 1976 |
| 98 | 43 | 576 | 772 |
| 99 | 45 | 575 | 1334 |
| 100 | 61 | 578 | 1863 |
| 101 | 62 | 557 | 1516 |

Example 102

The compounds of examples 14, 15, 16, 17, 19, 21 and 39 are weighed precisely in 0.1 mg-order and dissolved in 50 ml toluene (aerated) using volumetric flask to give exact solution molarity. Optical absorption spectra thereof are measured using HITACHI U-3300 spectrophotometer to evaluate molar absorption coefficient. The solutions are then precisely diluted by 10-times with aerated toluene using measuring pipette and volumetric flask. Optical absorption and photoluminescence spectra of the above diluted solutions are measured using U-3300 and HITACHI F-4500 fluorescence spectrophotometer, respectively, to evaluate FQY.

The above compounds are deposited on a slide glass substrate by vacuum evaporation under a reduced pressure of $6.665 \times 10^{-4}$ Pa ($5.0 \times 10^{-6}$ Torr) and at a depositing rate of 0.05 nm/sec to a film thickness of 50 nm to form a transparent film. Optical absorption and photoluminescence spectra of the films are evaluated using U-3300 and F-4500 spectrophotometer, respectively. The results are summarized in the table below. These compounds absorb the light of approximately 480 nm in both solution state and evaporated film and fluoresce in green region in solution and fluoresce in orange to red region in evaporated film. These properties prove that the compounds are applicable for color changing media described previously.

TABLE 8 use for color changing media

| compund of example | in toluene | | | | in evaporated film | |
|---|---|---|---|---|---|---|
| | $\lambda_{ma}^{*1}$, nm | $\epsilon^{*2}$ | $F_{max}^{*3}$, nm | $\Phi^{*4}$ | $\lambda_{max}^{*1}$, nm | $F_{max}^{*3}$, nm |
| 14 | 479 | 21480 | 531 | 0.65 | 478 | 598 |
| 15 | 474 | 23060 | 529 | 0.67 | 476 | 589 |
| 16 | 486 | 20150 | 529 | 0.65 | 484 | 592 |
| 17 | 474 | 10310 | 529 | 0.72 | 481 | 588 |
| 19 | 474 | 21870 | 530 | 0.61 | 480 | 586 |
| 21 | 476 | 22320 | 530 | 0.60 | 490 | 608 |
| 39 | 475 | 13950 | 528 | 0.65 | 480 | 581 |

*1 wavelength at optical absorption maximum
*2 molar absorption coefficient
*3 wavelength at photoluminescence maximum
*4 FQY Example 103 example 69 is repeated replacing the light-emitting material and the cathode with the film co-deposited using the compound described in example 34 and Rhodamine-19 (0.50 wt.-%) and the cathode co-deposited using magnesium and silver (Mg:Ag, 20:1), respectively. The co-deposition is done under a depositing condition of $6.665 \times 10^{-4}$ Pa ($5.0 \times 10^{-6}$ Torr) and 0.13 nm/s (1.3 Å/s) for the compound of example 34, 0.66 pm/s (0.0066 Å/s) for Rhodamine-19, 200 pm/s, (2.0 Å/s) for magnesium and 10 pm/s (0.1 Å/s) for silver. For comparison, the device employing the compound of example 34 for light-emitting substance is prepared using the cathode of Mg/Ag (20:1).

The device processing the co-deposited light-emitting layer begins to emit from at 4V. The wavelength of the EL emission spectrum is 558 nm. This suggests that the emission is induced via resonance energy transfer from the compound of example 34 to Rhodamine-19. The device of the single component light-emitting layer begins from at 7V with the maximum EL emission wavelength 529 nm. The EL emission performances are summarized in the table below.

| Bias voltage (V) | EL Intensity (cd/m$^2$) | |
|---|---|---|
| | Host-Guest type | Single component type |
| 12 | 290 | 12 |
| 13 | 600 | 36 |
| 14 | 1220 | 67 |
| 15 | 1900 | 135 |

The above results demonstrate that the invented compounds are useful for Host-Guest type light-emitting materials.

Example 104

28 g (0.25 mol) of potassium tert.-butoxide, 62.5 g (0.23 mol) of 4-(diphenylamino)benzonitrile and 300 ml of tert.-amyl alcohol are heated up to 100° C. under a nitrogen atmosphere. As soon as the this temperature has been reached, a solution of 26.7 g (0.12 mol) of di-n-butyl succinate and 70 ml of tert.-amyl alcohol is added over 1 hour using a dropping funnel. When the addition is completed, the reaction mixture is kept for 16 hours at 100° C., then cooled down to 65° C., neutralized with 20 ml of glacial acetic acid and boiled briefly at reflux temperature. The resultant pigment suspension is filtered at room temperature. The filter cake is suspended in 300 ml of methanol and the pigment is isolated again by filtration, then finally washed with methanol and water until washings run colourless, and dried at 100° C. in vacuo, affording 10.8 g (15% of theory, based on dibutyl succinate) of pure pigment of 1,4-diketo-3,6-bis-(4-diphenylaminophenyl)-pyrrolo-(3,4-c)-pyrrole.

1.02 g (1.64 mmol) 1,4-diketo-3,6-bis-(4-diphenylaminophenyl)-pyrrolo-(3,4-c)-pyrrole are slurred in 20 ml of 1-methyl-2-pyrrrolidinone for 2 hours at room temperature. 0.57 g (5.09 mmol) of potassium tert.-butoxide is added to the slurry under nitrogen. After stirring for 2 hours, 1.37 g (4.84 mmol) of 3,5di-t-butylbenzyl bromide are added to the reaction mixture and then the mixture is stirred additionally for 2 hours. After the reaction mixture is poured into 50 ml of water, the obtained solid is filtered off and purified by column chromatography (silica gel, dichloromethane as eluent). After drying, 0.444 g (26%) of a red solid are obtained.

The compound obtained above exhibits the optical properties summarized in the table below:

| in toluene | | | | in evaporated film | |
|---|---|---|---|---|---|
| $\lambda$max$^{*1}$ nm | $\epsilon^{*2}$ | Fmax$^{*3}$ nm | $\Phi^{*4}$ | $\lambda$max$^{*1}$ nm | Fmax$^{*3}$ nm |
| 533 | 47400 | 591 | 0.48 | 537 | 609 |

*1 wavelength at optical absorption maximum,
*2 molar absorption coeffcient
*3 wavelength at photoluminescence maximum,
*4 FQY Example 103 is then repeated for EL device preparation replacing the light-emitting material with the film co-deposited using tris-(8-hydroxyquinolinato)aluminum(III) (manufactured by Wako Pure Chemicals Industries, Ltd.) and the compound prepared above (0.50 wt.-%). The co-deposition is done under a depositing condition of $6.665 \times 10^{-4}$ Pa ($5.0 \times 10^{-6}$ Torr) and 300 pm/s (3.0 Å/s) for the aluminum complex and 1.5 pm/s (0.015 Å/s) for the above compound. For comparison, the device employing the aluminum complex for light-emitting substance is prepared.

The device using a light-emitting layer comprising of solely the aluminum complex begins to emit a green EL emission starting at 8 V. The emission maximum is at 520 nm with the intensity 6980 cd/m² at 25 V. The device using a light-emitting layer comprising the complex and the compound begins to emit from at 4 V (see the table below for the device performance). The wavelength of the EL emission maximum is at 590 nm, i.e. orange emission which is different from that of the single component device above. This suggests that the emission is induced via resonance energy transfer from the aluminum complex to the compound invented.

| Bias voltage (V) | EL Intensity (cd/m²) |
|---|---|
| 15 | 540 |
| 16 | 1300 |
| 17 | 3900 |
| 18 | 12520 |

The above results demonstrate that the invented compounds are useful for energy acceptor of Host-Guest type of light-emitting materials.

Example 105

2.09 g (4.75 mmol) 1,4-diketo-3,6-bis-(4-biphenyl)-pyrrolo-(3,4-c)-pyrrole are slurred in 30 ml of 1-methyl-2-pyrrolidinone for 2 hours at room temperature. 1.29 g (11.52 mmol) of potassium tert.-butoxide are added to the slurry under an atmosphere of nitrogen. After stirring for 1 hour, 1.21 g (10 mmol) of allyl bromide are added to the reaction mixture and then the mixture is stirred additionally for two hours. The mixture then is poured into 50 ml of water and the obtained red solid is filtered off and then purified by column chromatography (silica gel, dichloromethane as eluent). After drying, 1.13 g (60%) of a red solid are obtained.

Example 106

Example 105 is repeated except that 1,4-diketo-3,6-bis-(4-methylphenyl)-pyrrolo-(3,4-c)-pyrrole is used as starting material. A red solid (54%) is obtained.

Example 107

Example 105 is repeated except that 3,3-dimethylallyl bromide is used instead of allyl bromide. A red solid (42%) is obtained.

Example 108

Example 105 is repeated except that 3-phenylallyl bromide is used instead of allyl bromide. A red solid (55%) is obtained.

Example 109

A mixture of 45 g (0.4 mol) of potassium tert.-butoxide, 82 g (0.373 mol) of 9-ethyl-3-cyanocarbazole and 300 ml of tert.-amylalcohol is heated up to a temperature of 110° C. under a nitrogen atmosphere. As soon as this temperature is reached, a solution of 43 g (0.18 mol) of di-n-butyl succinate and 100 ml of tert.-amyl alcohol are added over 1.5 hours using a dropping funnel. When the addition is complete, the reaction mixture is kept for 16 hours at 110° C., then cooled to 65° C., neutralized with 40 ml glacial acetic acid and boiled briefly at reflux temperature. The resultant pigment suspension is filtered at room temperature. The filter cake is suspended in 300 ml of methanol and the pigment is isolated by filtration, then finally washed with methanol and water until washings run colorless, and dried at 100° C. under an atmosphere of reduced pressure. 10.5 g (11%) of pure 1,4-diketo-3,6-bis-(3-9-ethylcarbazole)-pyrrolo-(3,4-c)pyrrole are obtained.

Example 110

Example 105 is repeated except that 1,4-diketo-3,6-bis-(2-napthyl)-pyrrolo-(3,4-c)-pyrrole and 3,5-di-tert.-butylbenzylbromide are used. A red solid (36%) is obtained.

Example 111

Example 110 is repeated except that 3,5-dimethylbenzyl bromide is used instead of 3,5-di-tert.-butylbenzylbromide. A red solid (30%) is obtained.

Example 112

Example 109 is repeated except that 1-(4-cyanophenyl)-2-(3,5-di-tert.-butylphenyl)-trans-ethylene is used instead of 9-ethyl-3-cyanocarbazole. A red solid (5%) is obtained.

Example 113

Example 112 is repeated except that 3,5-dimethylbenzyl bromide is used as alkylating agent. A red solid (8%) is obtained.

Example 114

Example 10 is repeated except that 3-bromo benzyl bromide as alkylating agent. A red solid (23%) is obtained.

Example 115

Example 10 is repeated except that methyl iodide is used as alkylating agent. A red solid (40%) is obtained.

Example 116

Example 10 is repeated except that 3-methylbenzyl bromide is used as alkylating agent. A red solid (45%) is obtained.

Example 117

(a) 4.04 g (10 mmol) 1,4-diketo-3,6-bis-(4-biphenyl)-pyrrolo-(3,4-c)-pyrrole are slurred in 30 ml of 1-methyl-2-pyrrolidinone for two hours at room temperature. 1.23 g (11 mmol) of potassium tert.-butoxide are added to this slurry under a nitrogen atmosphere. After stirring for 1 hour, 2.83 g (10 mmol) of 3,5-di-tert.-butylbenzylbromide is added to the reaction mixture and then the mixture is stirred additionally for two hours. The mixture is poured into 50 ml of water and the red solid is filtered off and purified by column chromatography (silica gel, dichloromethane as eluent). After drying, 1.61 g (25%) 1,4-diketo-2-(di-tert.-butylbenzyl)-3,6-bis-(4-biphenyl)-pyrrolo-(3,4-c)-pyrrole are obtained.

(b) The obtained 1.61 g 1,4-diketo-2-(di-tert.-butylbenzyl)-3,6-bis-(4-biphenyl)-pyrrolo-(3,4-c)-pyrrole are slurred in 20 ml of 1-methyl-2-pyrrolidinone for 15 min. at room temperature. 0.32 g (2.8 mmol) of potassium tert.-butoxide are added to the slurry under a nitrogen atmosphere. After stirring for one hour, 3.38 g (1.2 mmol) of 1,2-diiodoethane are added to the reaction mixture and then the mixture is stirred additionally for two hours. Then the mixture is poured into 50 ml of water and the red solid is filtered off and purified by column chromatography (silica gel, dichloromethane as eluent). After drying, 0.58 g of a red solid of formula IV are obtained

Examples 119 to 129

Example 104 is repeated replacing only the guest material in the binary system with the compounds listed in Table 9 below, summarizing the EL performances also:

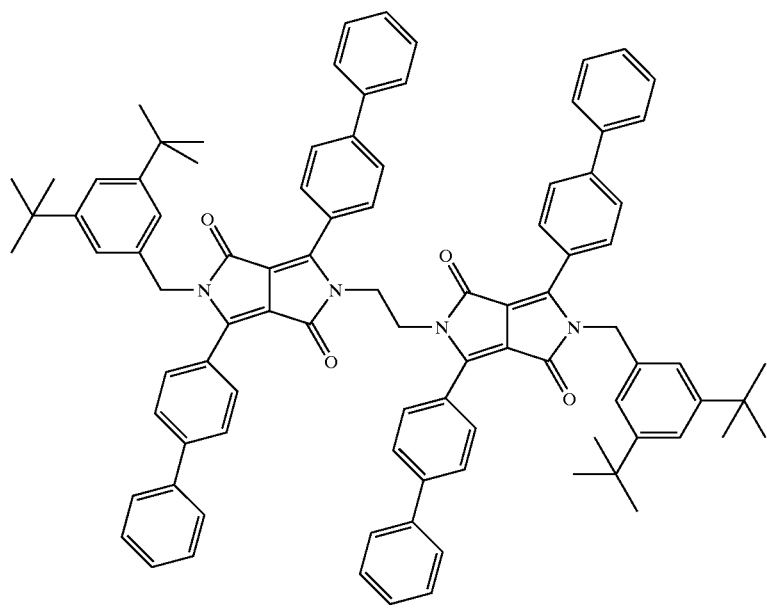

IV

Example 118

(a) Example 117 (a) is repeated except that 1,4-diketo-3,6-bis-(4-methylphenyl)-pyrrolo-(3,4-c)-pyrrole is used as starting compound and 1,4-diketo-2-(di-tert.-butylbenzyl)-3,6-bis-(4-methylphenyl)-pyrrolo-(3,4-c)-pyrrole is obtained (32%).

(b) Example 117 (b) is repeated except that 1,4-diketo-2-(di-tert.-butylbenzyl)-3,6-bis-(4-methylphenyl)-pyrrolo-(3,4-c)-pyrrole and a,a'-dibromo-p-xylene are used. A red solid of the following formula V

TABLE 9

| Example | Guest Material (example) | Guest Concentration [wt.-%] to $Alq_3$ | EL Emission Peak Wavelength [nm] | EL Intensity [$cd/m^2$] |
|---|---|---|---|---|
| 119 | 57 | 1.4 | 555 | 4820 |
| 120 | 53 | 1.2 | 594 | 8517 |
| 121 | 55 | 1.3 | 566 | 7329 |
| 122 | 59 | 1.8 | 591 | 5344 |

V

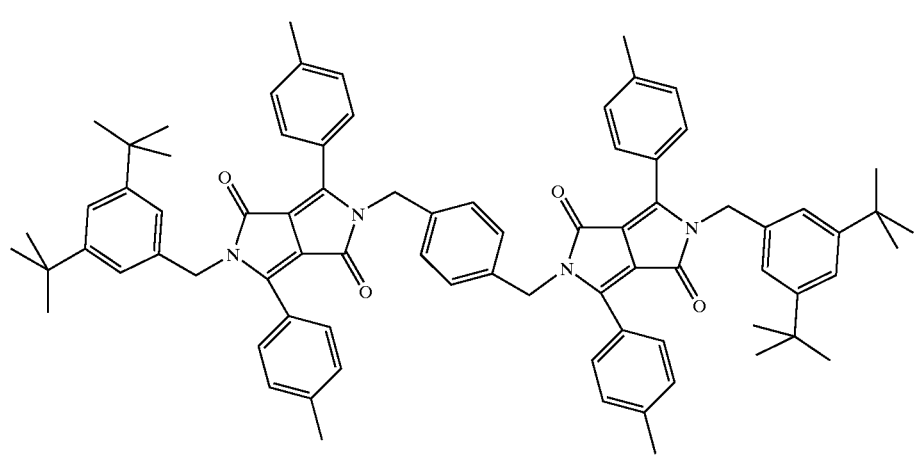

is obtained.

TABLE 9-continued

| Example | Guest Material (example) | Guest Concentration [wt.-%] to Alq$_3$ | EL Emission Peak Wavelength [nm] | EL Intensity [cd/m$^2$] |
|---|---|---|---|---|
| 123 | 104 | 1.3 | 608 | 11004 |
| 124 | 114 | 1.5 | 619 | 9831 |
| 125 | 109 | 1.3 | 567 | 8745 |
| 126 | 112 | 1.8 | 591 | 5302 |
| 127 | 115 | 1.4 | 611 | 6398 |
| 128 | 116 | 2 | 617 | 8784 |
| 129 | 10 | 2 | 621 | 7108 |

Examples 130 to 134

Example 69 is repeated replacing the light emitting material with the compounds listed in Table 10 below, summarizing the EL performances also:

TABLE 10

| Example | Guest Material (example) | EL Emission Peak Wavelength [nm] | EL Intensity [cd/m$^2$] |
|---|---|---|---|
| 130 | 105 | 639 | 1429 |
| 131 | 106 | 611 | 4540 |
| 132 | 109 | 588, 625 | 2330 |
| 133 | 112 | 605 | 1654 |
| 134 | 113 | 624 | 875 |

Example 135

294 mg of in tetrahydrofurane recrystallized Alq$_3$ (manufactured from Tokyo Kasei Organic Chemicals) and 6 mg of 1,4-diketo-2,5-bis-(3,5-di-tert.-butylbenzyl)-3,6-bis-(4-diphenylaminophenyl)-pyrrolo-(3,4-c)pyrrole are dissolved in 50 ml of dichloromethane. The thus obtained solution is slowly poured into 500 ml of hot water, and the thus obtained precipitate is collected and dried. The obtained precipitate is purified by means of sublimation with heating under an atmosphere of reduced pressure of $6.65 \cdot 10^{-4}$ Pa ($5 \cdot 10^{-6}$ Torr). 250 mg (5%) of a red host/guest composite are obtained.

Example 103 is then repeated for EL device preparation replacing the light-emitting material with the above obtained host/guest composite.

Examples 136 to 138

Example 136 is repeated without a replacement of the guest concentration listed in Table 11 below:

TABLE 11

| Example | Guest Concentration [wt.-%] | EL Emission Peak Wavelength [nm] | EL Intensity [cd/m$^2$] |
|---|---|---|---|
| 136 | 5 | 615 | 9013 |
| 137 | 3 | 617 | 10085 |
| 138 | 2 | 613 | 9686 |

The invention claimed is:
1. Electroluminescent device comprising in this order
(a) an anode
(b) a hole transporting layer
(c) a light-emitting layer
(d) optionally an electron transporting layer and
(e) a cathode and a light-emitting substance, wherein the light-emitting substance is a diketopyrrolopyrrole ("DPP") represented by formula I or formula III

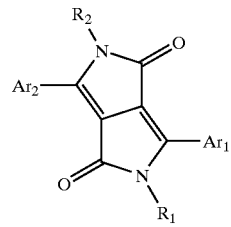

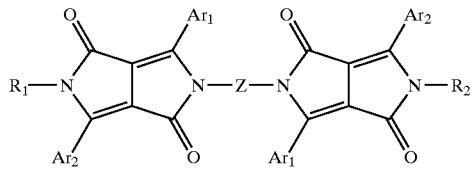

wherein $R_1$ and $R_2$, independently from each other, stand for $C_1$–$C_{25}$-alkyl, allyl which can be substituted one to three times with $C_1$–$C_3$alkyl or $Ar_3$, or —$CR_3R_4$—$(CH_2)_m$—$Ar_3$, wherein $R_3$ and $R_4$ independently from each other stand for hydrogen, $C_1$–$C_4$alkyl, or phenyl which can be substituted one to three times with $C_1$–$C_3$ alkyl, $Ar_3$ stands for phenyl or 1- or 2-naphthyl which can be substituted one to three times with $C_1$–$C_8$alkyl, $C_1$–$C_8$alkoxy, halogen or phenyl, which can be substituted with $C_1$–$C_8$alkyl or $C_1$–$C_8$alkoxy one to three times, and m stands for 0, 1, 2, 3 or 4, $Ar_1$ and $Ar_2$, independently from each other, stand for

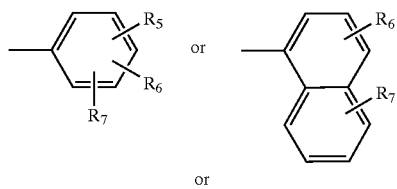

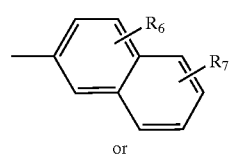

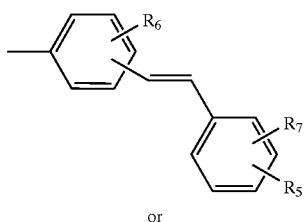

or

-continued

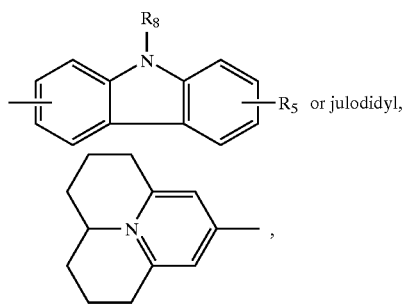

which can be substituted one to four times with $C_1$–$C_4$alkyl, $C_1$–$C_4$alkoxy, or phenyl or

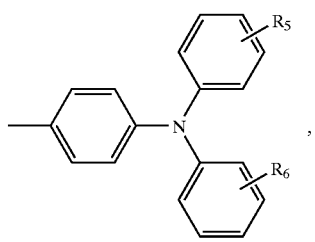

or phenanthryl, 2- or 9-fluorenyl, or anthracenyl,
wherein
$R_5$, $R_6$ and $R_7$, independently from each other, stand for hydrogen, cyano, halogen, $C_1$–$C_6$alkyl, —$NR_8R_9$, —$OR_{10}$, —$S(O)_nR_8$, —$Se(O)_nR_8$, or phenyl, which can be substituted one to three times with $C_1$–$C_8$alkyl or $C_1$–$C_8$alkoxy,
wherein $R_8$ and $R_9$, independently from each other, stand for hydrogen, phenyl, $C_1$–$C_{25}$-alkyl, $C_5$–$C_{12}$-cycloalkyl, —$CR_3R_4$—$(CH_2)_m$-Ph, $R_{10}$, wherein $R_{10}$ stands for $C_6$–$C_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, wherein Ph, the aryl and heterocyclic radical can be substituted one to three times with $C_1$–$C_8$alkyl, $C_1$–$C_8$alkoxy, or halogen, or $R_8$ and $R_9$ stand for —$C(O)R_{11}$, wherein $R_{11}$ can be $C_1$–$C_{25}$-alkyl, $C_5$–$C_{12}$-cycloalkyl, $R_{10}$, —$OR_{12}$ or —$NR_{13}R_{14}$, wherein $R_{12}$, $R_{13}$, and $R_{14}$ stand for $C_1$–$C_{25}$-alkyl, $C_5$–$C_{12}$-cycloalkyl, $C_6$–$C_{24}$-aryl,
or $R_5$, $R_6$ and $R_7$ stand for
a saturated or unsaturated heterocyclic radical comprising five to seven ring atoms, wherein the ring consists of carbon atoms and one to three hetero atoms selected from the group consisting of nitrogen, oxygen and sulfur, wherein the heterocyclic radical can be substituted one to three times with $C_1$–$C_8$alkyl or $C_1$–$C_8$alkoxy, or —$NR_8R_9$ stands for a five- or six membered heterocyclic radical in which $R_8$ and $R_9$ together stand for tetramethylene, pentamethylene, —$CH_2$—$CH_2$—O—$CH_2$—$CH_2$—, or —$CH_2$—$CH_2$—$NR_{50}$—$CH_2$—$CH_2$—, wherein $R_{50}$ stands for hydrogen, $C_1$–$C_6$alkyl, phenyl or phenyl substituted one to three times with $C_1$–$C_8$alkyl or $C_1$–$C_8$alkoxy
and n stands for 0, 1, 2 or 3,
and wherein Z stands for a diradical selected from the group consisting of a single bond, $C_2$–$C_6$alkylene, which can be substituted one to three times with $C_1$–$C_4$alkyl, $C_1$–$C_4$alkoxy, or phenyl, phenylene or naphthylene.

2. An electroluminescent device according to claim 1, where $R_8$ and $R_9$ together stand for —$CH_2$—$CH_2$—O—$CH_2$—$CH_2$—.

3. An electroluminescent device according to claim 1, where the diketopyrrolopyrrole of the formula I is:

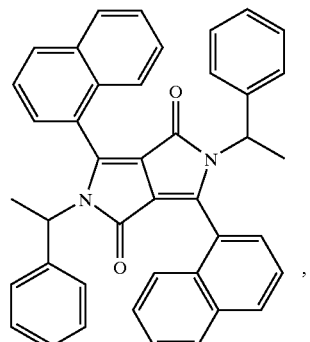

,

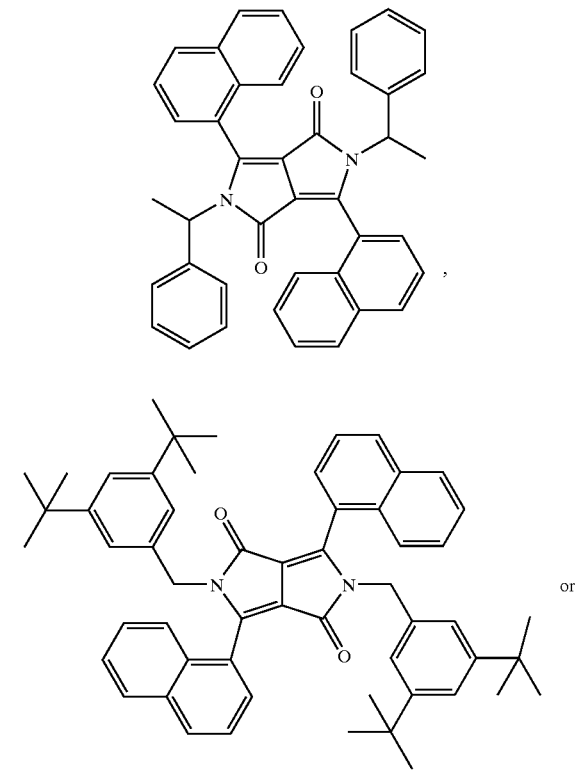

or

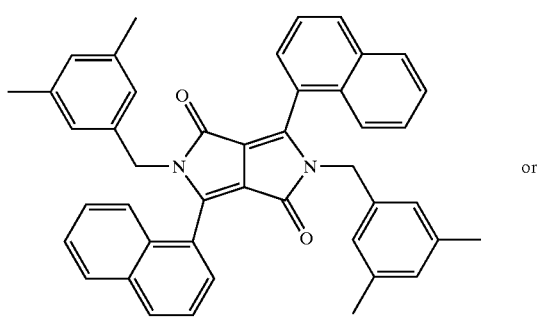

or

-continued

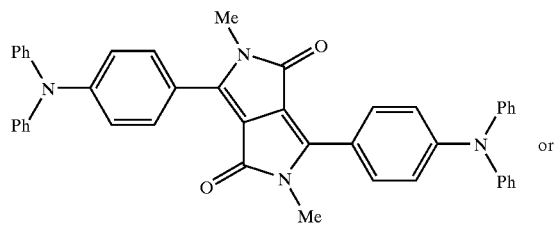

or

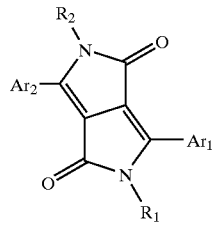

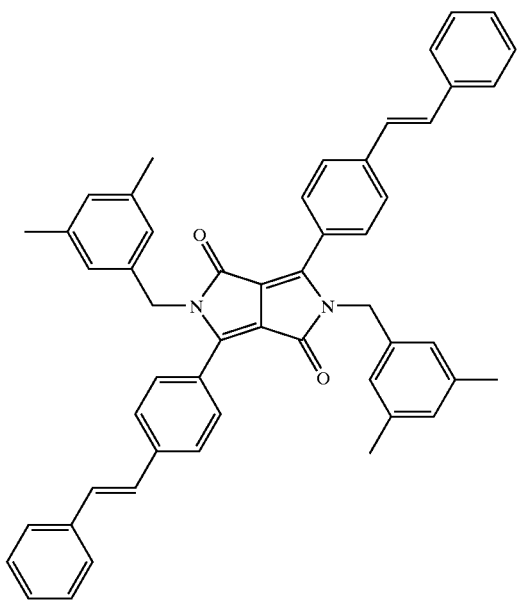

4. An electroluminescent device according to claim 1, wherein in the diketopyrrolopyrrole of the formula I $R_1$ and $R_2$ are $C_1$–$C_8$alkyl, $Ar_1$ and $Ar_2$ are a group of formula

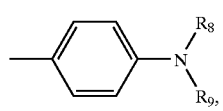

wherein $R_8$ and $R_9$ are phenyl.

5. An electroluminescent device comprising in this order
(a) an anode
(b) a hole transporting layer
(c) a light-emitting layer
(d) optionally an electron transporting layer and
(e) a cathode and a light-emitting substance, wherein the light-emitting substance is a diketopyrrolopyrrole ("DPP") represented by formula I

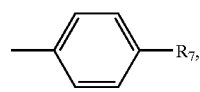

wherein
$R_1$ and $R_2$ are $C_1$–$C_8$alkyl, or —$(CH_2)_m$-Ph, $Ar_1$ and $Ar_2$ are a group of formula

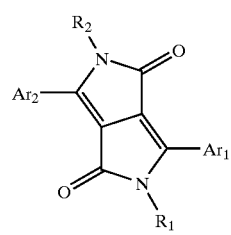

wherein $R_7$ is —$N(R_8)_2$, wherein $R_8$ is unsubstituted or substituted phenyl, unsubstituted or substituted heterocyclic radical or $C_5$–$C_{12}$-cycloalkyl, and m stands for 0, 1, 2, 3 or 4.

6. An electroluminescent device comprising in this order
(a) an anode
(b) a hole transporting layer
(c) a light-emitting layer
(d) optionally an electron transporting layer and
(e) a cathode and a light-emitting substance, wherein the light-emitting substance is a diketopyrrolopyrrole ("DPP") represented by formula I

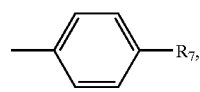

wherein
$R_1$ and $R_2$ are —$CH_2$-Ph, wherein phenyl can be substituted with phenyl, naphthyl or $C_1$–$C_4$alkyl up to two times, $Ar_1$ and $Ar_2$ are a group of formula

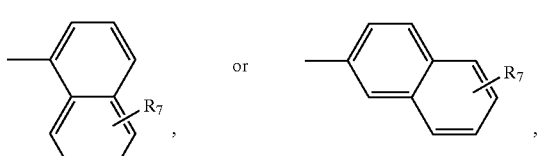

wherein $R_7$ is hydrogen or OMe.

7. An electroluminescent device according to claim 6, where the diketopyrrolopyrrole of the formula I is:
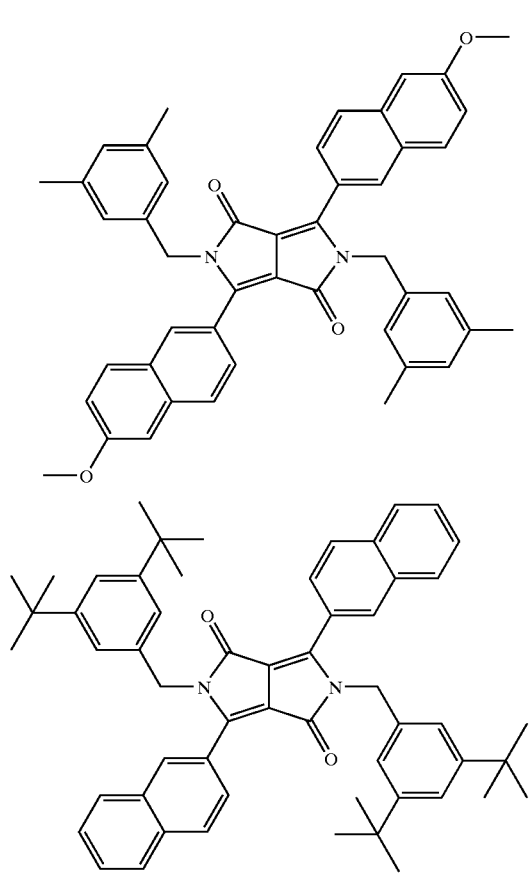
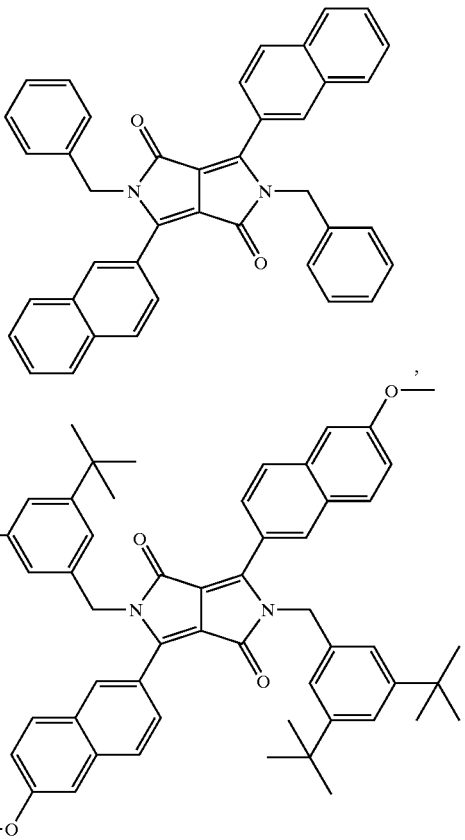
* * * * *

UNITED STATES PATENT AND TRADEMARK OFFICE
CERTIFICATE OF CORRECTION

PATENT NO. : 7,001,677 B2
DATED : February 21, 2006
INVENTOR(S) : Junji Otani et al.

It is certified that error appears in the above-identified patent and that said Letters Patent is hereby corrected as shown below:

Column 52,
Lines 45-50, should read:

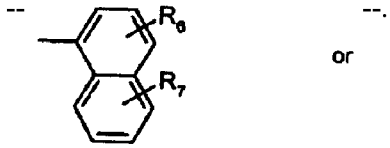

Signed and Sealed this

Thirteenth Day of June, 2006

JON W. DUDAS
*Director of the United States Patent and Trademark Office*